(12) United States Patent
Boutell et al.

(10) Patent No.: US 11,634,765 B2
(45) Date of Patent: Apr. 25, 2023

(54) METHODS AND COMPOSITIONS FOR PAIRED END SEQUENCING USING A SINGLE SURFACE PRIMER

(71) Applicant: Illumina Cambridge Limited, Cambridge (GB)

(72) Inventors: Jonathan Mark Boutell, Cambridge (GB); Pietro Gatti-Lafranconi, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 307 days.

(21) Appl. No.: 16/717,303

(22) Filed: Dec. 17, 2019

(65) Prior Publication Data
US 2020/0190578 A1    Jun. 18, 2020

Related U.S. Application Data

(60) Provisional application No. 62/781,273, filed on Dec. 18, 2018.

(51) Int. Cl.
*C12Q 1/6874* (2018.01)
*C12N 15/10* (2006.01)

(52) U.S. Cl.
CPC ....... *C12Q 1/6874* (2013.01); *C12N 15/1093* (2013.01)

(58) Field of Classification Search
None
See application file for complete search history.

(56) References Cited

U.S. PATENT DOCUMENTS

| | | |
|---|---|---|
| 7,754,429 B2 | 7/2010 | Rigatti et al. |
| 7,790,418 B2 | 9/2010 | Mayer |
| 8,017,335 B2 | 9/2011 | Smith |
| 8,143,008 B2 | 3/2012 | Kawashima et al. |
| 8,192,930 B2 | 6/2012 | Vermaas et al. |
| 9,029,103 B2 | 5/2015 | Rigatti et al. |
| 9,139,874 B2 | 9/2015 | Myers et al. |
| 9,453,258 B2 | 9/2016 | Kain et al. |
| 2004/0057917 A1 | 3/2004 | Wolf et al. |
| 2010/0035269 A1 | 2/2010 | Ma et al. |
| 2010/0129874 A1 | 5/2010 | Mitra et al. |

(Continued)

FOREIGN PATENT DOCUMENTS

| | | |
|---|---|---|
| DE | 19812103 | 9/1999 |
| EP | 3260554 | 12/2017 |
| WO | WO 2007/010251 | 1/2007 |

(Continued)

OTHER PUBLICATIONS

International Search Report and Written Opinion for PCT/EP2019/084183, issued by the European Patent Office, dated Feb. 21, 2020; 14 pgs.

(Continued)

*Primary Examiner* — Kaijiang Zhang
(74) *Attorney, Agent, or Firm* — Mueting Raasch Group

(57) ABSTRACT

The present disclosure is concerned with compositions and methods for the paired-end sequencing of target nucleic acids, and more particularly to obtaining nucleotide sequence information from two separate regions of target nucleic acids using amplification sites having a single type of surface primer.

30 Claims, 5 Drawing Sheets

(56) References Cited

U.S. PATENT DOCUMENTS

2012/0156728 A1   6/2012  Li et al.
2020/0181686 A1   6/2020  Boutell et al.

FOREIGN PATENT DOCUMENTS

WO    WO-2014031163 A1 *  2/2014  ........... C12Q 1/6869
WO    WO 2016/075204       5/2016

OTHER PUBLICATIONS

Ma et al., "Isothermal amplification method for next-generation sequencing," PNAS, Aug. 27, 2013; 110 (35):14320-14323.
Ma et al., "WildFire: A Simple Monoclonal Colony Generation Technology without Emulsion PCR," LifeTechnologies, 2012, [Online] obtained May 12, 2012 at http://assets.thermofisher.com/TFS-Assets/LSG/brochures/5500-wildfire-ashg-poster.pdf.
International Search Report and Written Opinion for PCT/EP2019/083173, issued by the European Patent Office, 14 pgs.
International Preliminary Report on Patentability for PCT/EP2019/083173, dated Jun. 21, 2021, 7 pages.
Lehman and Nussbaum, "The Deoxyribonucleases of *Escherichia coli*, V. On the Specificity of Exonuclease I (Phosphodiesterase)," Journal of Biological Chem, Aug. 1054;239(8): 2628-2636.

* cited by examiner

METHODS AND COMPOSITIONS FOR PAIRED END SEQUENCING USING A SINGLE SURFACE PRIMER

PRIORITY

This application claims the benefit of U.S. Provisional Application No. 62/781,273, filed Dec. 18, 2018, the disclosure of which is incorporated by reference herein in its entirety.

FIELD

The present disclosure relates to, among other things, the paired-end sequencing of target nucleic acids, and more particularly to obtaining nucleotide sequence information from two separate regions of target nucleic acids using amplification sites having a single population of surface primer.

BACKGROUND

Next-generation sequencing (NGS) technology relies on the highly parallel sequencing of monoclonal populations of amplicons that were produced from a single target nucleic acid. NGS methods have greatly increased sequencing speed and data output, resulting in the massive sample throughput of current sequencing platforms. Further reduction of the time for sequencing a template is highly desirable, but it is necessary to maintain useful signal-to-noise ratios, intensity, and increased percentage of clusters that pass filter, all of which contribute to increased data output and data quality.

Cluster generation has proven very useful in the preparation of a library. It typically includes production of a library where the members of the library include a universal sequence present at each end. The library is loaded into a flow cell and individual members of the library are captured on a lawn of surface-bound oligos complementary to the universal sequence. Each member is then amplified into distinct clonal clusters through bridge amplification.

Sequencing of templates in a cluster often includes the technique of "paired-end" or "pairwise" sequencing (U.S. Pat. No. 8,017,335). Paired-end sequencing is a multi-step process that allows the determination of two "reads" of sequence from two places on a single template. The advantage of the paired-end approach is that there is significantly more information to be gained from sequencing two stretches each of bases from a single template than from sequencing the same number of bases from each of two independent templates in a random fashion. With the use of appropriate software tools for the assembly of sequence information it is possible to make use of the knowledge that the "paired-end" sequences are not completely random, but are known to occur on a single template, and are therefore linked or paired in the genome. This information has been shown to greatly aid the assembly of whole genome sequences into a consensus sequence.

SUMMARY OF THE APPLICATION

Provided herein is a method for paired-end sequencing of target nucleic acids that significantly reduces the time required for sequencing of target nucleic acids present on amplification sites of an array. Standard methods typically include the use of amplification sites with two populations of surface primers, determining the sequence of one strand, and then taking several steps accomplish the turnaround typically used in paired-end sequencing. In contrast, the method provided herein does not require the turnaround. Instead, an amplification site with one surface primer is used, and the number of steps to obtain sequence data from both strands is reduced. This method provides for a percentage of clusters passing filter that is comparable to standard methods, and a percentage of clusters passing filter that is higher than standard methods when longer inserts are used.

The method allows sequencing of two regions of the target nucleic acid, referred to herein as the first and second regions, for sequence determination. The first and second regions for sequence determination are on complementary strands of the target nucleic acid, which are referred to herein respectively as first and second templates. The two regions for sequence determination may or may not be complementary to each other. Standard methods for sequencing two regions of a target nucleic acid often include a paired-end turn, e.g., the use of an amplification site with two different surface primers, also referred to herein as capture nucleic acids, and formation of one template followed by formation of a second template. As described in detail herein, the paired-end turn is not used. Instead, methods include the advantage of using amplification sites populated with a single surface primer.

Provided herein are methods for pairwise sequencing of first and second regions of a target nucleic acid, where the first and second regions are in complementary strands of the target nucleic acid. In one embodiment, the method includes providing an array comprising a plurality of amplification sites. The amplification sites include a plurality of capture nucleic acids, and a plurality of clonal single-stranded amplicons. Each single-stranded amplicon is attached at its 5' end to a capture nucleic acid, and the capture nucleic acids include a cleavage site. The method also includes hybridizing a first sequencing primer to a universal sequence present on each single-stranded amplicon and carrying out a first sequencing reaction. The first sequencing reaction includes the sequential addition of nucleotides to the first sequencing primer using the single-stranded amplicon as a first template. The sequencing reaction results in identifying the sequence of a first region and producing a complementary strand of the first region. The complementary strand is extended to form a double-stranded amplicon that includes the first sequencing primer, nucleotides incorporated during the sequencing reaction, and nucleotides incorporated during the extending of the complementary strand.

The method also includes cleaving the capture nucleic acid attached to the single-stranded amplicons. The cleavage converts the single-stranded amplicons into shortened capture nucleic acids and unattached first templates that are not attached at the 5' end to the capture nucleic acid. A second sequencing reaction is carried out by sequential addition of nucleotides to a second sequencing primer hybridized to the complementary strand and using the complementary strand as a second template to determine the sequence of a second region.

Also provided herein are compositions. In one embodiment, a composition includes an array of amplification sites. The amplification sites include a plurality of clonal double-stranded amplicons. Each double-stranded amplicon includes a first strand attached to the surface of the amplification site by the 5' end, and a second strand that is not attached to the surface of the amplification site and having nucleotides that are complementary to and hybridized to nucleotides of the first strand. The first strand has a break in the backbone, where the break in the backbone of the first strand is flanked on both sides by complementary nucleotides of the second strand.

Definitions

Terms used herein will be understood to take on their ordinary meaning in the relevant art unless specified otherwise. Several terms used herein and their meanings are set forth below.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon can be produced by any of a variety of amplification methods that use the nucleic acid, e.g., a target nucleic acid or an amplicon thereof, as a template including, for example, polymerase extension, polymerase chain reaction (PCR), rolling circle amplification (RCA), ligation extension, or ligation chain reaction. An amplicon can be a nucleic acid molecule having a single copy of a particular nucleotide sequence (e.g. a polymerase extension product) or multiple copies of the nucleotide sequence (e.g. a concatemeric product of RCA). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As used herein, the term "amplification site" refers to a site in or on an array where one or more amplicons can be generated. An amplification site can be further configured to contain, hold or attach at least one amplicon that is generated at the site.

As used herein, the term "array" refers to a population of sites that can be differentiated from each other according to relative location. Different molecules that are at different sites of an array can be differentiated from each other according to the locations of the sites in the array. An individual site of an array can include one or more molecules of a particular type. For example, a site can include a single target nucleic acid molecule having a particular sequence or a site can include several nucleic acid molecules having the same sequence (and/or complementary sequence, thereof). The sites of an array can be different features located on the same substrate. Exemplary features include without limitation, wells in a substrate, beads (or other particles) in or on a substrate, projections from a substrate, ridges on a substrate or channels in a substrate. The sites of an array can be separate substrates each bearing a different molecule. Different molecules attached to separate substrates can be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term "capacity," when used in reference to a site and nucleic acid material, means the maximum amount of nucleic acid material, e.g., amplicons derived from a target nucleic acid, that can occupy the site. For example, the term can refer to the total number of nucleic acid molecules that can occupy the site in a particular condition. Other measures can be used as well including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

As used herein, the term "capture agent" refers to a material, chemical, molecule, or moiety thereof that is capable of attaching, retaining, or binding to a target molecule (e.g. a target nucleic acid). Exemplary capture agents include, without limitation, a capture nucleic acid that is complementary to at least a portion of a modified target nucleic acid (e.g., a universal capture binding sequence), a member of a receptor-ligand binding pair (e.g. avidin, streptavidin, biotin, lectin, carbohydrate, nucleic acid binding protein, epitope, antibody, etc.) capable of binding to a modified target nucleic acid (or linking moiety attached thereto), or a chemical reagent capable of forming a covalent bond with a modified target nucleic acid (or linking moiety attached thereto). In one embodiment, a capture agent is a nucleic acid. A nucleic acid capture agent can also be used as an amplification primer or a sequencing primer.

The terms "P5" and "P7" may be used when referring to a nucleic acid capture agent. The terms "P5'" (P5 prime) and "P7'" (P7 prime) refer to the complement of P5 and P7, respectively. It will be understood that any suitable nucleic acid capture agent can be used in the methods presented herein, and that the use of P5 and P7 are exemplary embodiments only. Uses of nucleic acid capture agents such as P5 and P7 on flowcells is known in the art, as exemplified by the disclosures of WO 2007/010251, WO 2006/064199, WO 2005/065814, WO 2015/106941, WO 1998/044151, and WO 2000/018957. One of skill in the art will recognize that a nucleic acid capture agent can also function as an amplification primer or a sequencing primer. For example, any suitable nucleic acid capture agent can act as a forward amplification primer, whether immobilized or in solution, and can be useful in the methods presented herein for hybridization to a sequence (e.g., a universal capture binding sequence) and amplification of a sequence. Similarly, any suitable nucleic acid capture agent can act as a reverse amplification primer, whether immobilized or in solution, and can be useful in the methods presented herein for hybridization to a sequence (e.g., a universal capture binding sequence) and amplification of a sequence. Further, as described herein a nucleic acid capture agent can also function as a sequencing primer. For example, any suitable nucleic acid capture agent or a portion thereof can act as a sequencing primer, whether immobilized or in solution, and can be useful in the methods presented herein for hybridization to a sequence (e.g., a universal capture binding sequence) and sequencing of the nucleotides located 3' of the primer. In view of the general knowledge available and the teachings of the present disclosure, one of skill in the art will understand how to design and use sequences that are suitable for capture and amplification of target nucleic acids as presented herein.

As used herein, the term "universal sequence" refers to a region of sequence that is common to two or more target nucleic acids, where the molecules also have regions of sequence that differ from each other. A universal sequence that is present in different members of a collection of molecules can allow capture of multiple different nucleic acids using a population of capture nucleic acids that are complementary to a portion of the universal sequence, e.g., a universal capture binding sequence. Non-limiting examples of universal capture binding sequences include sequences that are identical to or complementary to P5 and P7 primers. Similarly, a universal sequence present in different members of a collection of molecules can allow the replication or amplification of multiple different nucleic acids using a population of universal primers that are complementary to a portion of the universal sequence, e.g., a universal primer binding site. Target nucleic acid molecules may be modified to attach universal adapters (also referred to herein as adapters), for example, at one or both ends of the different target sequences, as described herein.

As used herein, the term "adapter" and its derivatives, e.g., universal adapter, refers generally to any linear oligonucleotide which can be ligated to a target nucleic acid. In some embodiments, the adapter is substantially non-complementary to the 3' end or the 5' end of any target sequence present in a sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some aspects the adapter can include one or more cleavable groups at one or more locations. In another aspect, the adapter can include a sequence that is substantially identical, or substantially complementary, to at least a portion of a primer, for example a capture nucleic acid. In some embodiments, the adapter can include a barcode, also referred to as an index or tag, to assist with downstream error correction, identification, or sequencing. The terms "adaptor" and "adapter" are used interchangeably.

As defined herein, "sample" and its derivatives is used in its broadest sense and includes any specimen, culture and the like that is suspected of including a target nucleic acid. In some embodiments, the sample comprises DNA, RNA, PNA, LNA, chimeric or hybrid forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some embodiments, the source of nucleic acid material can include nucleic acids obtained from a newborn, for example as typically used for newborn screening.

As used herein, the terms "clonal" and "monoclonal" are used interchangeably and refer to a population of nucleic acids that is homogeneous with respect to a particular nucleotide sequence. The homogenous sequence is typically at least 10 nucleotides long, but can be even longer including for example, at least 50, at least 100, at least 250, at least 500, or at least 1000 nucleotides long. A clonal population can be derived from a single target nucleic acid. Typically, all of the nucleic acids in a clonal population will have the same nucleotide sequence. It will be understood that a small number of mutations (e.g. due to amplification artifacts) can occur in a clonal population without departing from clonality. It will also be understood that a small number of different target nucleic acid (e.g., due to a target nucleic acid that was not amplified or amplified to a limited degree) can occur in a clonal population without departing from clonality.

As used herein, the term "different," when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other. As used herein, the term "different," when used in reference to amplification sites, means that the amplification sites are present at distinct separate locations on the same array.

As used herein, the term "fluidic access," when used in reference to a molecule in a fluid and a site in contact with the fluid, refers to the ability of the molecule to move in or through the fluid to contact or enter the site. The term can also refer to the ability of the molecule to separate from or exit the site to enter the solution. Fluidic access can occur when there are no barriers that prevent the molecule from entering the site, contacting the site, separating from the site and/or exiting the site. However, fluidic access is understood to exist even if diffusion is retarded, reduced or altered so long as access is not absolutely prevented.

As used herein, the term "double stranded," when used in reference to a nucleic acid molecule, means that substantially all of the nucleotides in the nucleic acid molecule are hydrogen bonded to a complementary nucleotide. A partially double stranded nucleic acid can have at least 10%, at least 25%, at least 50%, at least 60%, at least 70%, at least 80%, at least 90% or at least 95% of its nucleotides hydrogen bonded to a complementary nucleotide.

As used herein, the term "each," when used in reference to a collection of items, is intended to identify an individual item in the collection but does not necessarily refer to every item in the collection unless the context clearly dictates other.

As used herein, the term "interstitial region" refers to an area in a substrate or on a surface that separates other areas of the substrate or surface. For example, an interstitial region can separate one feature of an array from another feature of the array. The two regions that are separated from each other can be discrete, lacking contact with each other. In another example, an interstitial region can separate a first portion of a feature from a second portion of a feature. The separation provided by an interstitial region can be partial or full separation. Interstitial regions will typically have a surface material that differs from the surface material of the features on the surface. For example, features of an array can have an amount or concentration of capture agents that exceeds the amount or concentration present at the interstitial regions. In some embodiments the capture agents may not be present at the interstitial regions.

As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. As described in detail herein, polymerases can be used during an amplification to produce clonal clusters, can be used during a sequencing reaction to determine the sequence of a nucleic acid, and different polymerases can be used in each of these aspects. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bsu (*Bacillus subtilis*), Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "nucleic acid" is intended to be consistent with its use in the art and includes naturally occurring nucleic acids and functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art. Naturally occurring nucleic acids generally have a deoxyribose sugar (e.g. found in deoxyribonucleic acid (DNA)) or a ribose sugar (e.g. found in ribonucleic acid (RNA)). A nucleic acid can contain any of a variety of analogs of these sugar moieties that are known in the art. A nucleic acid can include native or non-native bases. In this regard, a native deoxyribonucleic acid can have one or more bases selected from adenine, thymine, cytosine or guanine and a ribonucleic acid can have one or more bases selected from uracil, adenine, cytosine or guanine. Useful non-native bases that can be included in a nucleic acid are known in the art. The term "target," when used in reference to a nucleic acid, is intended as a semantic identifier for the nucleic acid in the context of a method or composition set forth herein and does not necessarily limit the structure or function of the nucleic acid beyond what is otherwise explicitly indicated. A target nucleic acid having a universal sequence at each end, for instance a universal adapter at each end, can be referred to as a modified target nucleic acid.

As used herein, the term "transport" refers to movement of a molecule through a fluid. The term can include passive transport such as movement of molecules along their concentration gradient (e.g. passive diffusion). The term can also include active transport whereby molecules can move along their concentration gradient or against their concentration gradient. Thus, transport can include applying energy to move one or more molecule in a desired direction or to a desired location such as an amplification site.

As used herein, the term "rate," when used in reference to transport, amplification, capture or other chemical processes, is intended to be consistent with its meaning in chemical kinetics and biochemical kinetics. Rates for two processes can be compared with respect to maximum rates (e.g. at saturation), pre-steady state rates (e.g. prior to equilibrium), kinetic rate constants, or other measures known in the art. In particular embodiments, a rate for a particular process can be determined with respect to the total time for completion of the process. For example, an amplification rate can be determined with respect to the time taken for amplification to be complete. However, a rate for a particular process need not be determined with respect to the total time for completion of the process.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Conditions that are "suitable" for an event to occur, such as exonuclease-mediated digestion of a nucleic acid, or "suitable" conditions are conditions that do not prevent such events from occurring. Thus, these conditions permit, enhance, facilitate, and/or are conducive to the event.

As used herein, "providing" in the context of a composition, an article, or a nucleic acid, means making the composition, article, or nucleic acid, purchasing the composition, article, or nucleic acid, or otherwise obtaining the compound, composition, article, nucleic acid.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

In the description herein particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The following detailed description of illustrative embodiments of the present disclosure may be best understood when read in conjunction with the following drawings.

Figure 2:
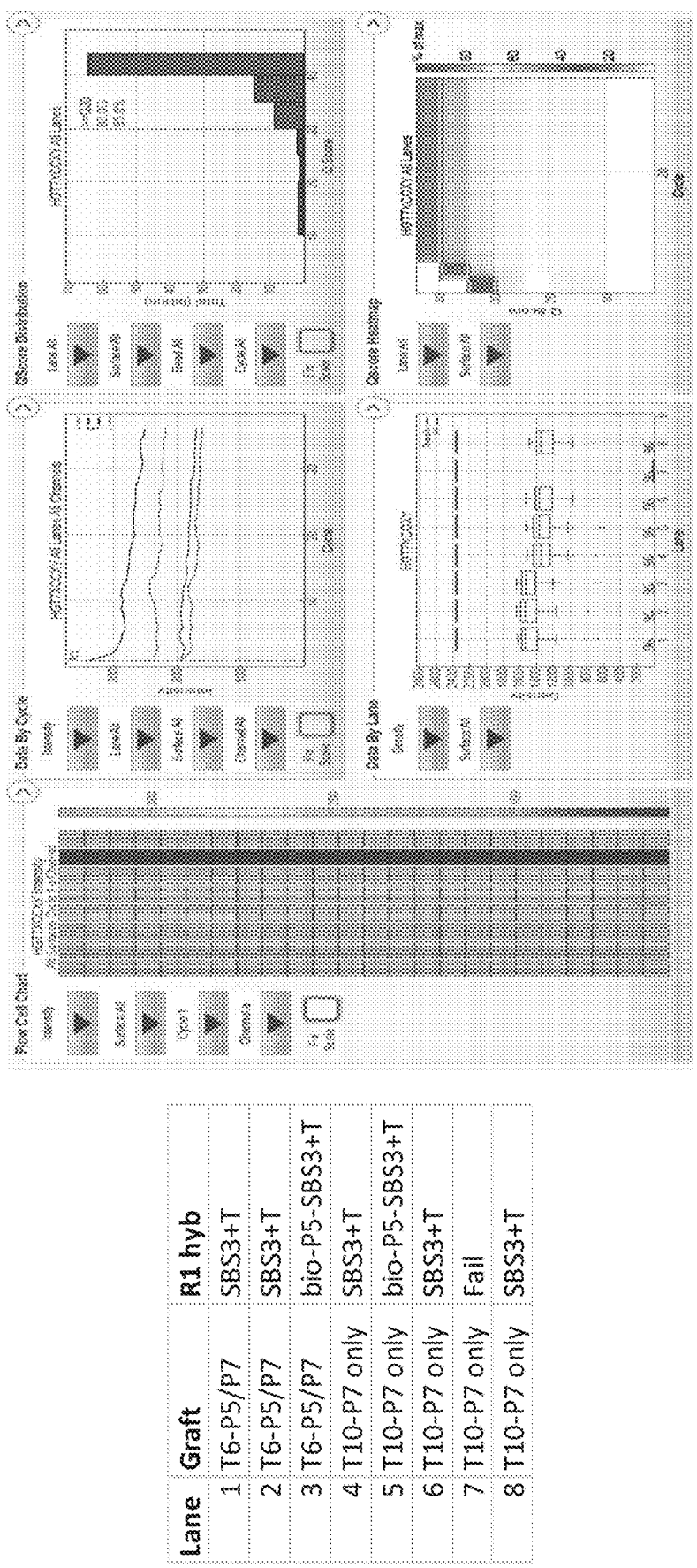
Figure 3:
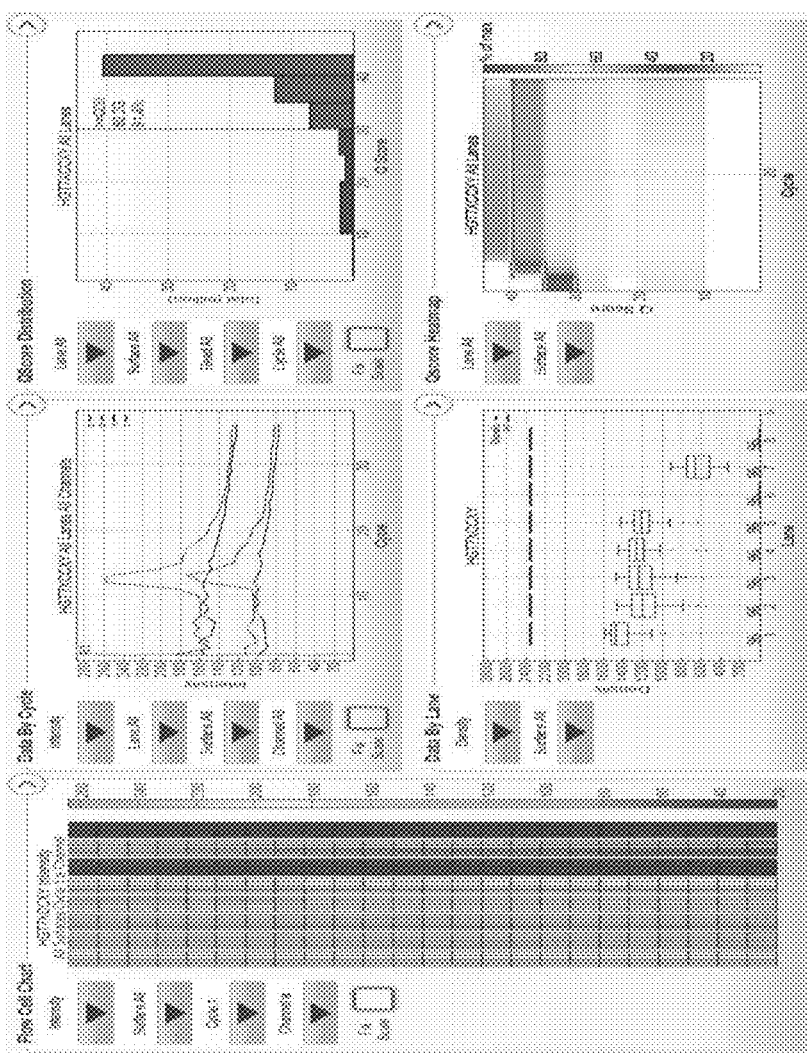
Figure 5:
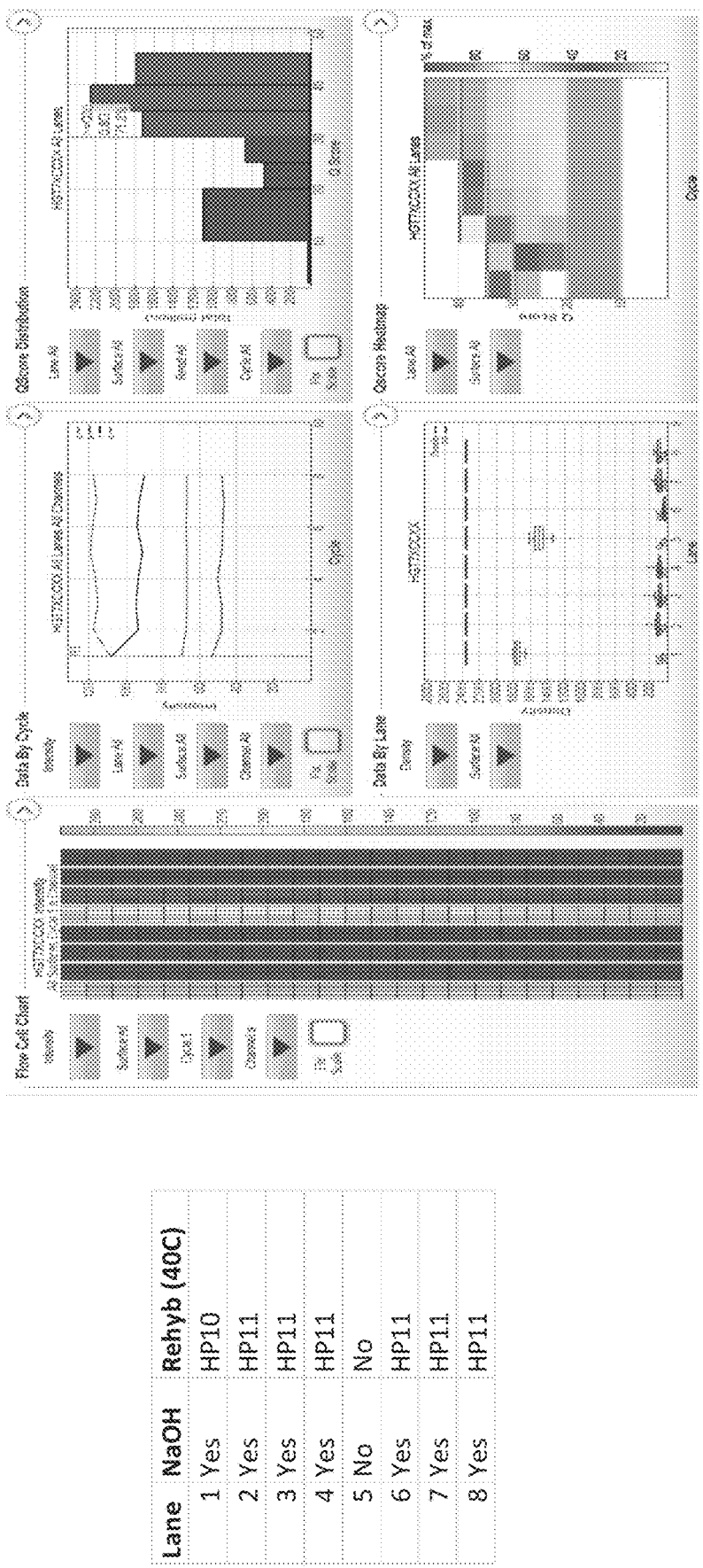

For FIGS. 2, 3, and 5: the panel labelled "Flow Cell Chart" shows the flowcell with lanes 1-8 from left to right; the panel labelled "Data by Cycle" shows the progression of quality metrics during the run; the panel labelled "Data by Lane" shows the quality metrics per lane; the panel labelled "QScore Distribution" shows the number of reads by quality score; and the panel labelled "QScore Heatmap" shows the Q-score by cycle.

FIG. 2 shows results of read 1 (R1) sequencing of single primer amplification sites. The left panel shows the primer(s) attached to the surface of amplification sites and the R1 primer used for sequencing in each lane of a flowcell. "Graft" refers to the surface primer(s) (also referred to herein as capture nucleic acids) attached to the surface of the amplification sites. T6-P5/P7 refers to lanes with both P5 and P7 surface primers attached, and T10-P7 only refers to lanes with P7 surface primers. "R1 hyb" refers to the R1 sequencing primer used. SBS3+T is a standard R1 primer, and Bio-P5-SBS3+T is the primer with dual biotin added.

FIG. 3 shows results of processing the flowcell from Example 2 for read 2 (R2) sequencing. The left panel shows the primer(s) attached to the surface of amplification sites and the R1 primer used for sequencing in each lane of a flowcell and is identical to FIG. 2. The left panel also shows the additional treatments of each lane of the flowcell. "Extend/Nick" refers to treatment with Bst amplification mix and FpG to cleave one strand; "Kinase" refers to treatment with kinase; "Dehyb?" refers to whether, and how, the unattached strand was removed; and ""R2" hyb (40)" refers to the R2 primer used.

Figure 4B:
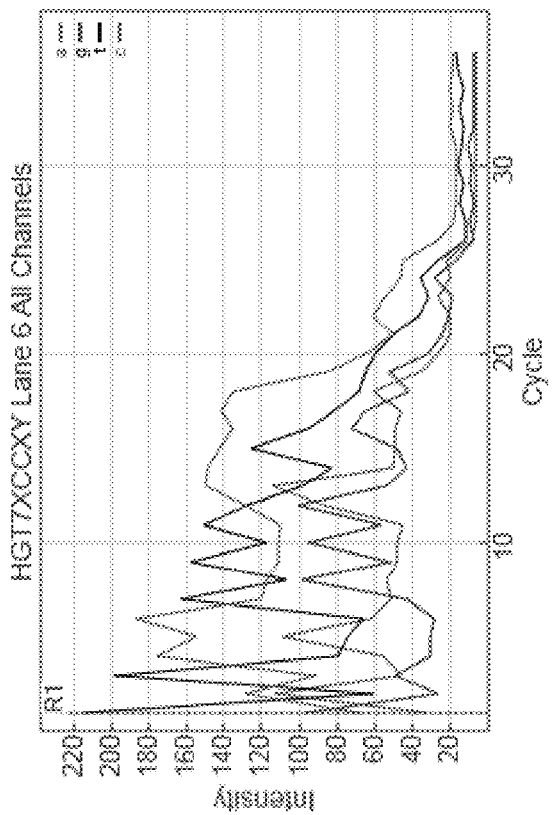
Figure 4A:
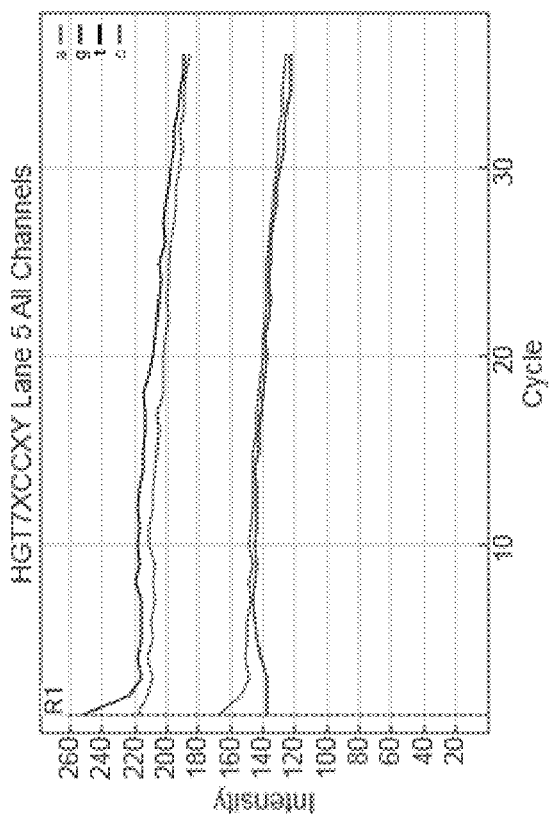

FIG. 4 shows the data by cycle of lane 5 (FIG. 4A) and lane 6 (FIG. 4B) of the results presented in FIG. 3.

FIG. 5 shows the results of processing the flowcell from Example 3 for sequencing with R2 after dehybridization. The left panel shows lanes as described in FIGS. 2 and 3 and the additional treatment with NaOH to denature the double-stranded amplicons and the R2 primer used for the additional sequencing reaction.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Figure 1A:
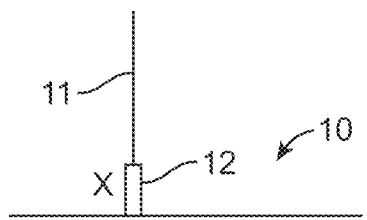
FIGS. 1A-1G show schematic drawings of an embodiment of preparing a target nucleic acid for sequencing according to various aspects of the disclosure presented herein. For simplicity, only one amplicon is shown.

Presented herein are methods and compositions related to sequencing nucleic acids. The present disclosure provides methods for pairwise sequencing of first and second regions of a target nucleic acid, where the first and second regions are in complementary strands. In one embodiment, the method includes providing an array that includes a plurality of amplification sites. Each amplification site includes a plurality of capture nucleic acids attached by the 5' end to the amplification site. The capture nucleic acids include a cleavage site. Each amplification site also includes a plurality of clonal single-stranded amplicons, where each single-stranded amplicon is attached at its 5' end to a capture nucleic acid and the 3' end of the single-stranded amplicon is not attached to the surface of the amplification site. One population of capture nucleic acid is present. For instance, in FIG. 1A an amplification site 10 is shown with one member of a plurality of single-stranded amplicons 11 attached to a capture nucleic acid 12. Also shown in FIG. 1A is the cleavage site, marked with an X on capture nucleic acid 12.

Figure 1B:
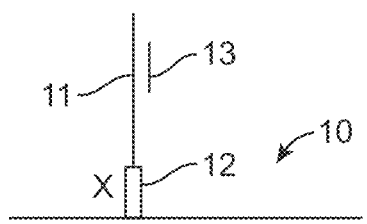

The method further includes hybridizing a sequencing primer to the single-stranded amplicon. For instance, in FIG. 1B a sequencing primer 13 annealed to the single-stranded amplicon 11. A first sequencing reaction is carried out by sequential addition of nucleotides to the 3' end of the sequencing primer. The sequencing primer is used by a DNA polymerase to initiate synthesis, and the single-stranded amplicon acts as the first template. The result of the sequencing reaction is to determine the sequence of a first region and to produce a complementary strand of the first region. For instance, in FIG. 1C the sequencing primer 13 annealed to the single-stranded amplicon 11 has been extended during the sequencing reaction and integrated into the resulting complementary strand 14 of the first region to result in a partially double-stranded structure 15.

The complementary strand is extended further, forming a double-stranded amplicon that is the complement of most of the single-stranded amplicon, and includes the first sequencing primer, nucleotides incorporated during the sequencing reaction, and the nucleotides incorporated during the extension of the complementary strand. For instance, in FIG. 1D the extended complementary strand 16 includes the nucleotides of the first sequencing primer, the nucleotides incorporated during the sequencing reaction, and the nucleotides incorporated during the extension.

The method further includes cleaving the capture nucleic acid attached to the single-stranded amplicon. For instance, as shown in FIG. 1E, the cleavage site X is cleaved leaving a cleaved strand 11' that is no longer attached to the array and a shortened capture nucleic acid 12'.

Figure 1E:
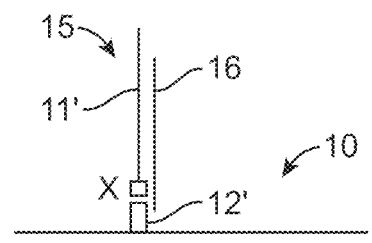

In one embodiment, the method can also include subjecting the structure illustrated in FIG. 1E to denaturing conditions to remove the portion of the cleaved strand (11' in FIG. 1D) not attached to the array. This results in the extended complementary strand 16 being single-stranded over most of its length. A second sequencing primer (17 in FIG. 1F) can be annealed to the extended complementary strand 16 and used for the second sequencing reaction where the extended complementary strand 16 is used as a second template.

In another embodiment, the shortened capture nucleic acid 12' can be used as a primer to initiate a sequencing reaction. When the shortened capture nucleic acid 12' is used as the sequencing primer, the removal of the cleaved strand (11' in FIG. 1E) not attached to the array is optional. Use of a DNA polymerase with strand displacement activity can initiate sequencing from the shortened capture nucleic acid and displace the cleaved strand during synthesis. In some embodiments, it may be necessary to modify the 3' end of the shortened capture nucleic acid to terminate in a 3'-OH. For instance, in FIG. 1G the extension 18 of the shortened capture nucleic acid 12' with a strand displacing DNA polymerase results in displacement of the cleaved strand 11'.

Arrays

An array of amplification sites used in a method set forth herein can be present as one or more substrates. Exemplary types of substrate materials that can be used for an array include glass, modified glass, functionalized glass, inorganic glasses, microspheres (e.g. inert and/or magnetic particles), plastics, polysaccharides, nylon, nitrocellulose, ceramics, resins, silica, silica-based materials, carbon, metals, an optical fiber or optical fiber bundles, polymers and multiwell (e.g. microtiter) plates. Exemplary plastics include acrylics, polystyrene, copolymers of styrene and other materials, polypropylene, polyethylene, polybutylene, polyurethanes and Teflon™. Exemplary silica-based materials include silicon and various forms of modified silicon.

In particular embodiments, a substrate can be within or part of a vessel such as a well, tube, channel, cuvette, Petri plate, bottle, or the like. A particularly useful vessel is a flow-cell, for example, as described in U.S. Pat. No. 8,241,573 or Bentley et al., Nature 456:53-59 (2008). Exemplary flow-cells are those that are commercially available from Illumina, Inc. (San Diego, Calif.). Another particularly useful vessel is a well in a multiwell plate or microtiter plate.

In some embodiments, the amplification sites of an array can be configured as features on a surface. The features can be present in any of a variety of desired formats. For example, the sites can be wells, pits, channels, ridges, raised regions, pegs, posts or the like. In one embodiment, the amplification sites can contain beads. However, in particular embodiments the sites need not contain a bead or particle. Exemplary sites include wells that are present in substrates used for commercial sequencing platforms sold by 454 LifeSciences (a subsidiary of Roche, Basel Switzerland) or Ion Torrent (a subsidiary of Life Technologies, Carlsbad, Calif., USA). Other substrates having wells include, for example, etched fiber optics and other substrates described in U.S. Pat. Nos. 6,266,459; 6,355,431; 6,770,441; 6,859,570; 6,210,891; 6,258,568; 6,274,320; 8,262,900; 7,948,015; U.S. Pat. Pub. No. 2010/0137143; U.S. Pat. No. 8,349,167, or PCT Publication No. WO 00/63437. In several cases the substrates are exemplified in these references for applications that use beads in the wells. The well-containing substrates can be used with or without beads in the methods or compositions of the present disclosure. In some embodiments, wells of a substrate can include gel material (with or without beads) as set forth in U.S. Pat. No. 9,512,422.

The amplification sites of an array can be metal features on a non-metallic surface such as glass, plastic or other materials exemplified herein. A metal layer can be deposited on a surface using methods known in the art such as wet plasma etching, dry plasma etching, atomic layer deposition, ion beam etching, chemical vapor deposition, vacuum sputtering, or the like. Any of a variety of commercial instruments can be used as appropriate including, for example, the FlexAL®, OpAL®, Ionfab 300Plus®, or Optofab 3000® systems (Oxford Instruments, UK). A metal layer can also be deposited by e-beam evaporation or sputtering as set forth in Thornton, Ann. Rev. Mater. Sci. 7:239-60 (1977). Metal layer deposition techniques, such as those exemplified herein, can be combined with photolithography techniques to create metal regions or patches on a surface. Exemplary methods for combining metal layer deposition techniques and photolithography techniques are provided in U.S. Pat. Nos. 8,778,848 and 8,895,249.

An array of features can appear as a grid of spots or patches. The features can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful. The pitch can be the same between different pairs of nearest neighbor features or the pitch can vary between different pairs of nearest neighbor features. In particular embodiments, features of an array can each have an area that is larger than about 100 nm$^2$, 250 nm$^2$, 500 nm$^2$, 1 μm$^2$, 2.5 μm$^2$, 5 μm$^2$, 10 μm$^2$, 100 μm$^2$, or 500μ$^2$. Alternatively, or additionally, features of an array can each have an area that is smaller than about 1 mm$^2$, 500 μm$^2$, 100μ$^2$, 25 μm$^2$, 10 μm$^2$, 5 μm$^2$, 1 μm$^2$, 500 nm$^2$, or 100 nm$^2$. Indeed, a region can have a size that is in a range between an upper and lower limit selected from those exemplified above.

For embodiments that include an array of features on a surface, the features can be discrete, being separated by interstitial regions. The size of the features and/or spacing between the regions can vary such that arrays can be high density, medium density, or lower density. High density arrays are characterized as having regions separated by less than about 15 μm. Medium density arrays have regions separated by about 15 to 30 μm, while low density arrays have regions separated by greater than 30 μm. An array useful in the disclosure can have regions that are separated by less than 100 μm, 50 μm, 10 μm, 5 μm, 1 μm, or 0.5 μm.

In particular embodiments, an array can include a collection of beads or other particles. The particles can be suspended in a solution or they can be located on the surface of a substrate. Examples of bead arrays in solution are those commercialized by Luminex (Austin, Tex., USA). Examples of arrays having beads located on a surface include those wherein beads are located in wells such as a BeadChip array (Illumina Inc., San Diego, Calif., USA) or substrates used in sequencing platforms from 454 LifeSciences (a subsidiary of Roche, Basel, Switzerland) or Ion Torrent (a subsidiary of Life Technologies, Carlsbad, Calif. USA). Other arrays having beads located on a surface are described in U.S. Pat. Nos. 6,266,459; 6,355,431; 6,770,441; 6,859,570; 6,210,891; 6,258,568; 6,274,320; U.S. Pat. Pub. No. 2009/0026082 A1; U.S. Pat. Pub. No. 2009/0127589 A1; U.S. Pat. Pub. No. 2010/0137143 A1; U.S. Pat. Pub. No. 2010/0282617 A1; or PCT Publication No. WO 00/63437. Several of the above references describe methods for attaching target nucleic acids to beads prior to loading the beads in or on an array substrate. It will be understood, however, that the beads can be made to include amplification primers and the beads can then be used to load an array, thereby forming amplification sites for use in a method set forth herein. As set forth previously herein, the substrates can be used without beads. For example, amplification primers can be attached directly to the wells or to gel material in wells. Thus, the references are illustrative of materials, compositions or apparatus that can be modified for use in the methods and compositions set forth herein.

Amplification sites of an array can include a plurality of capture agents capable of binding to target nucleic acids. In one embodiment, a capture agent includes a capture nucleic acid. The nucleotide sequence of the capture nucleic acid is complementary to a universal sequence of the target nucleic acids. In some embodiments, the capture nucleic acid can also function as a primer for amplification of the target nucleic acid. In some embodiments, one population of capture nucleic acid includes a P5 primer or the complement thereof. In some embodiments, the amplification sites also include a plurality of a second capture nucleic acid, and this second capture nucleic acid can include a P7 primer or the complement thereof. In some embodiments a capture nucleic acid can include a cleavage site. Cleavage sites in a capture nucleic acid are described in greater detail herein.

In particular embodiments, a capture agent, such as a capture nucleic acid, can be attached to the amplification sites. For example, the capture agent can be attached to the surface of a feature of an array. The attachment can be via an intermediate structure such as a bead, particle or gel. An example of attachment of capture nucleic acids to an array via a gel is described in U.S. Pat. No. 8,895,249 and further exemplified by flow cells available commercially from Illumina Inc. (San Diego, Calif., USA) or described in WO 2008/093098. Exemplary gels that can be used in the methods and apparatus set forth herein include, but are not limited to, those having a colloidal structure, such as agarose; polymer mesh structure, such as gelatin; or cross-linked polymer structure, such as polyacrylamide, SFA (see, for example, US Pat. App. Pub. No. 2011/0059865 A1) or PAZAM (see, for example, U.S. Pat. No. 9,012,022). Attachment via a bead can be achieved as exemplified in the description and cited references set forth previously herein.

In some embodiments, the features on the surface of an array substrate are non-contiguous, being separated by interstitial regions of the surface. Interstitial regions that have a substantially lower quantity or concentration of capture agents, compared to the features of the array, are advantageous. Interstitial regions that lack capture agents are particularly advantageous. For example, a relatively small amount or absence of capture moieties at the interstitial regions favors localization of target nucleic acids, and subsequently generated clusters, to desired features. In particular embodiments, the features can be concave features in a surface (e.g. wells) and the features can contain a gel material. The gel-containing features can be separated from each other by interstitial regions on the surface where the gel is substantially absent or, if present the gel is substantially incapable of supporting localization of nucleic acids. Methods and compositions for making and using substrates having gel containing features, such as wells, are set forth in U.S. Pat. No. 9,512,422.

Target Nucleic Acids

An array used in a method described herein includes double-stranded modified target nucleic acids. The terms "target nucleic acid," "target fragment," "target nucleic acid fragment, "target molecule," and "target nucleic acid molecule" are used interchangeably to refer to nucleic acid molecules where identification of its nucleotide sequence is desired. The target nucleic acid may be essentially any nucleic acid of known or unknown sequence. It may be, for example, a fragment of genomic DNA or cDNA. Sequencing may result in determination of the sequence of the whole or a part of the target molecule. The targets can be derived from a primary nucleic acid sample that has been randomly fragmented. In one embodiment, the targets can be processed into templates suitable for amplification by the placement of universal amplification sequences, e.g., sequences present in a universal adaptor, at the ends of each target fragment. A target nucleic acid having a universal adapter at each end can be referred to as a "modified target nucleic acid." Universal adapters are detailed herein.

The primary nucleic acid sample may originate in double-stranded DNA (dsDNA) form (e.g. genomic DNA fragments, PCR and amplification products and the like) from a sample or may originate in single-stranded form from a sample, as DNA or RNA, and been converted to dsDNA form. By way of example, mRNA molecules may be copied into double-stranded cDNAs suitable for use in a method described herein using standard techniques well known in the art. The precise sequence of the polynucleotide molecules from a primary nucleic acid sample is generally not material to the disclosure, and may be known or unknown.

In one embodiment, the primary polynucleotide molecules from a primary nucleic acid sample are DNA molecules. More particularly, the primary polynucleotide molecules represent the entire genetic complement of an organism, and are genomic DNA molecules which include both intron and exon sequences, as well as non-coding regulatory sequences such as promoter and enhancer sequences. In one embodiment, particular subsets of polynucleotide sequences or genomic DNA can be used, such as, for example, particular chromosomes. Yet more particularly, the sequence of the primary polynucleotide molecules is not known. Still yet more particularly, the primary polynucleotide molecules are human genomic DNA molecules. The DNA target fragments may be treated chemically or enzymatically either prior or subsequent to any random fragmentation processes, and prior or subsequent to the ligation of the universal adapter sequences.

The nucleic acid sample can include high molecular weight material such as genomic DNA (gDNA). The sample can include low molecular weight material such as nucleic acid molecules obtained from formalin-fixed paraffin-embedded or archived DNA samples. In another embodiment, low molecular weight material includes enzymatically or mechanically fragmented DNA. The sample can include cell-free circulating DNA. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample. In some embodiments, the sample can include nucleic acid molecules obtained from an animal such as a human or mammalian source. In another embodiment, the sample can include nucleic acid molecules obtained from a non-mammalian source such as a plant, a bacterium, a virus, or a fungus. In some embodiments, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one embodiment, forensic samples can include nucleic acids obtained from a crime scene, from a missing persons DNA database, from a laboratory associated with a forensic investigation, or from forensic samples obtained by law enforcement agencies, one or more military services, or any such personnel. The nucleic acid sample may be a purified sample or a crude DNA containing lysate, for example derived from a buccal swab, paper, fabric or other substrate that may be impregnated with saliva, blood, or other bodily fluids. As such, in some embodiments, the nucleic acid sample may include low amounts of, or fragmented portions of DNA, such as genomic DNA. In some embodiments, target sequences can be present in one or more bodily fluids including but not limited to, blood, sputum, plasma, semen, urine, and serum. In some embodiments, target sequences can be obtained from hair, skin, tissue samples, autopsy, or remains of a victim. In some embodiments, nucleic acids including one or more target sequences can be obtained from a deceased animal or human. In some embodiments, target sequences can include nucleic acids obtained from non-human DNA such a microbial, plant or entomological DNA.

In some embodiments, target sequences or amplified target sequences are directed to purposes of human identification. In some embodiments, a method described herein can be used for identifying characteristics of a forensic sample. In some embodiments, a method described herein can be used for human identification methods using one or more target specific primers or one or more target specific primers designed using known primer design criteria. In one embodiment, a forensic or human identification sample containing at least one target sequence can be amplified using any one or more target-specific primers using known primer criteria.

Additional non-limiting examples of sources of biological samples can include whole organisms as well as a sample obtained from a patient. The biological sample can be obtained from any biological fluid or tissue and can be in a variety of forms, including liquid fluid and tissue, solid tissue, and preserved forms such as dried, frozen, and fixed forms. The sample may be of any biological tissue, cells, or fluid. Such samples include, but are not limited to, sputum, blood, serum, plasma, blood cells (e.g., white cells), ascitic fluid, urine, saliva, tears, sputum, vaginal fluid (discharge), washings obtained during a medical procedure (e.g., pelvic or other washings obtained during biopsy, endoscopy or surgery), tissue, nipple aspirate, core or fine needle biopsy samples, cell-containing body fluids, free floating nucleic acids, peritoneal fluid, and pleural fluid, or cells therefrom. Biological samples may also include sections of tissues such as frozen or fixed sections taken for histological purposes or micro-dissected cells or extracellular parts thereof. In some embodiments, the sample can be a blood sample, such as, for example, a whole blood sample. In another example, the sample is an unprocessed dried blood spot sample. In yet another example, the sample is a formalin-fixed paraffin-embedded sample. In yet another example, the sample is a saliva sample. In yet another example, the sample is a dried saliva spot sample.

Exemplary biological samples from which target nucleic acids can be derived include, for example, those from a eukaryote, for instance a mammal, such as a rodent, mouse, rat, rabbit, guinea pig, ungulate, horse, sheep, pig, goat, cow, cat, dog, primate, human or non-human primate; a plant, such as *Arabidopsis thaliana*, corn, sorghum, oat, wheat, rice, canola, or soybean; an algae, such as *Chlamydomonas reinhardtii*; a nematode such as *Caenorhabditis elegans*; an insect, such as *Drosophila melanogaster*, mosquito, fruit fly, honey bee or spider; a fish, such as zebrafish; a reptile; an amphibian, such as a frog or *Xenopus laevis*; a *Dictyostelium discoideum*; a fungi, such as *Pneumocystis carinii, Takifugu rubripes*, yeast, such as *Saccharamoyces cerevisiae* or *Schizosaccharomyces pombe*; or *Plasmodium falciparum*. Target nucleic acids can also be derived from a prokaryote such as a bacterium, *Escherichia coli*, staphylococci or *Mycoplasma pneumoniae*; an archaeon; a virus such as Hepatitis C virus or human immunodeficiency virus; or a viroid. Target nucleic acids can be derived from a homogeneous culture or population of organisms or alternatively from a collection of several different organisms, for example, in a community or ecosystem.

Random fragmentation refers to the fragmentation of a polynucleotide molecule from a primary nucleic acid sample in a non-ordered fashion by enzymatic, chemical, or mechanical methods. Such fragmentation methods are known in the art and use standard methods (Sambrook and Russell, Molecular Cloning, A Laboratory Manual, third edition). In one embodiment, fragmentation can be accomplished using a process often referred to as tagmentation. Tagmentation uses a transposome complex and combines into a single step fragmentation and ligation to add universal adapters (Gunderson et al., WO 2016/130704). For the sake of clarity, generating smaller fragments of a larger piece of nucleic acid via specific PCR amplification of such smaller fragments is not equivalent to fragmenting the larger piece of nucleic acid because the larger piece of nucleic acid sequence remains in intact (i.e., is not fragmented by the PCR amplification). Moreover, random fragmentation is designed to produce fragments irrespective of the sequence identity or position of nucleotides comprising and/or surrounding the break. More particularly, the random fragmentation is by mechanical means such as nebulization or sonication to produce fragments of about 50 base pairs in length to about 1500 base pairs in length, still more particularly 50-700 base pairs in length, yet more particularly 50-400 base pairs in length. Most particularly, the method is used to generate smaller fragments of from 50-150 base pairs in length Fragmentation of polynucleotide molecules by mechanical means (nebulization, sonication, and Hydroshear, for example) results in fragments with a heterogeneous mix of blunt and 3'- and 5'-overhanging ends. It is therefore desirable to repair the fragment ends using methods or kits (such as the Lucigen DNA terminator End Repair Kit) known in the art to generate ends that are optimal for insertion, for example, into blunt sites of cloning vectors. In a particular embodiment, the fragment ends of the population of nucleic acids are blunt ended. More particularly, the fragment ends are blunt ended and phosphorylated. The phosphate moiety can be introduced via enzymatic treatment, for example, using polynucleotide kinase.

A population of target nucleic acids can have an average strand length that is desired or appropriate for a particular application of the methods or compositions set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for a population of target nucleic acids can be in a range between a maximum and minimum value set forth herein. It will be understood that amplicons generated at an amplification site (or otherwise made or used herein) can have an average strand length that is in a range between an upper and lower limit selected from those exemplified above.

In some cases, a population of target nucleic acids can be produced under conditions or otherwise configured to have a maximum length for its members. For example, the maximum length for the members that are used in one or more steps of a method set forth herein or that are present in a particular composition can be less than 100,000 nucleotides, less than 50,000 nucleotides, less than 10,000 nucleotides, less than 5,000 nucleotides, less than 1,000 nucleotides, less than 500 nucleotides, less than 100 nucleotides, or less than 50 nucleotides. Alternatively or additionally, a population of target nucleic acids can be produced under conditions or otherwise configured to have a minimum length for its members. For example, the minimum length for the members that are used in one or more steps of a method set forth herein or that are present in a particular composition can be more than 10 nucleotides, more than 50 nucleotides, more than 100 nucleotides, more than 500 nucleotides, more than 1,000 nucleotides, more than 5,000 nucleotides, more than 10,000 nucleotides, more than 50,000 nucleotides, or more than 100,000 nucleotides. The maximum and minimum strand length for target nucleic acids in a population can be in a range between a maximum and minimum value set forth above. It will be understood that amplicons generated at an amplification site (or otherwise made or used herein) can have maximum and/or minimum strand lengths in a range between the upper and lower limits exemplified above.

In a particular embodiment, the target fragment sequences are prepared with single overhanging nucleotides by, for example, activity of certain types of DNA polymerase such as Taq polymerase or Klenow exo minus polymerase which has a non-template-dependent terminal transferase activity that adds a single deoxynucleotide, for example, deoxyadenosine (A) to the 3' ends of a DNA molecule, for example, a PCR product. Such enzymes can be used to add a single nucleotide 'A' to the blunt ended 3' terminus of each strand of the double-stranded target fragments. Thus, an 'A' could be added to the 3' terminus of each end repaired strand of the double-stranded target fragments by reaction with Taq or Klenow exo minus polymerase, while the universal adapter polynucleotide construct could be a T-construct with a compatible 'T' overhang present on the 3' terminus of each region of double stranded nucleic acid of the universal adapter. This end modification also prevents self-ligation of both vector and target such that there is a bias towards formation of target nucleic acids having a universal adapter at each end.

In some cases, the target nucleic acids that are derived from such sources can be amplified prior to use in a method or composition herein. Any of a variety of known amplification techniques can be used including, but not limited to, polymerase chain reaction (PCR), rolling circle amplification (RCA), multiple displacement amplification (MDA), or random prime amplification (RPA). It will be understood that amplification of target nucleic acids prior to use in a method or composition set forth herein is optional. As such, target nucleic acids will not be amplified prior to use in some embodiments of the methods and compositions set forth herein. Target nucleic acids can optionally be derived from synthetic libraries. Synthetic nucleic acids can have native DNA or RNA compositions or can be analogs thereof.

Universal Adapters

A target nucleic acid used in a method or composition described herein includes a universal adapter attached to each end. A target nucleic acid having a universal adapter at each end can be referred to as a "modified target nucleic acid." Methods for attaching a universal adapter to each end of a target nucleic acid used in a method described herein are known to the person skilled in the art. The attachment can be through standard library preparation techniques using ligation (U.S. Pat. Pub. No. 2018/0305753), or through tagmentation using transposase complexes (Gunderson et al., WO 2016/130704).

In one embodiment, double-stranded target nucleic acids from a sample, e.g., a fragmented sample, are treated by first ligating identical universal adaptor molecules ("mismatched adaptors," the general features of which are defined below, and further described in Gormley et al., U.S. Pat. No. 7,741,463, and Bignell et al., U.S. Pat. No. 8,053,192) to the 5' and 3' ends of the double-stranded target nucleic acids. In one embodiment, the universal adaptor includes the universal capture binding sequences necessary for immobilizing the target nucleic acids on an array for subsequent sequencing. In another embodiment, a PCR step is used to further modify the universal adapter present at each end of target nucleic acids prior to immobilizing and sequencing. For instance, an initial primer extension reaction is carried out using a universal primer binding site in which extension products complementary to both strands of each individual target nucleic acid are formed and add a universal capture binding sequence. The resulting primer extension products, and optionally amplified copies thereof, collectively provide a library of modified target nucleic acids that can be immobilized and then sequenced. The term "library" refers to the collection of target nucleic acids containing known common sequences at their 3' and 5' ends, and may also be referred to as a 3' and 5' modified library.

The universal adapters used in the method of the disclosure are referred to as "mismatched" adaptors because, as is explained in detail herein, the adaptors include a region of sequence mismatch, i.e., they are not formed by annealing fully complementary polynucleotide strands.

Mismatched adaptors for use herein are formed by annealing two partially complementary polynucleotide strands to provide, when the two strands are annealed, at least one double-stranded region, also referred to as a region of double stranded nucleic acid, and at least one unmatched single-stranded region, also referred to as a region of single-stranded non-complementary nucleic acid strands.

The double-stranded region of the universal adapter is a short double-stranded region, typically including 5 or more consecutive base pairs, formed by annealing the two partially complementary polynucleotide strands. This term refers to a double-stranded region of nucleic acid in which the two strands are annealed and does not imply any particular structural conformation.

It is generally advantageous for the double-stranded region to be as short as possible without loss of function. In this context, "function" refers to the ability of the double-stranded region to form a stable duplex under standard reaction conditions for an enzyme-catalyzed nucleic acid ligation reaction, which will be well known to the skilled reader (e.g., incubation at a temperature in the range of 4° C. to 25° C. in a ligation buffer appropriate for the enzyme), such that the two strands forming the universal adapter remain partially annealed during ligation of the universal adapter to a target molecule. It is not absolutely necessary for the double-stranded region to be stable under the conditions typically used in the annealing steps of primer extension or PCR reactions.

The double-stranded region of the universal adapters is typically identical in all universal adapters used in a ligation. Because universal adapters are ligated to both ends of each target molecule, the modified target nucleic acid will be flanked by complementary sequences derived from the double-stranded region of the universal adapters. The longer the double-stranded region, and hence the complementary sequences derived therefrom in the modified target nucleic acid constructs, the greater the possibility that the modified target nucleic acid construct is able to fold back and base-pair to itself in these regions of internal self-complementarity under the annealing conditions used in primer extension and/or PCR. It is, therefore, generally preferred for the double-stranded region to be 20 or less, 15 or less, or 10 or less base pairs in length in order to reduce this effect. The stability of the double-stranded region may be increased, and hence its length potentially reduced, by the inclusion of non-natural nucleotides which exhibit stronger base-pairing than standard Watson-Crick base pairs.

In one embodiment, the two strands of the universal adapter are 100% complementary in the double-stranded region. It will be appreciated that one or more nucleotide mismatches may be tolerated within the double-stranded region, provided that the two strands are capable of forming a stable duplex under standard ligation conditions.

Universal adaptors for use herein will generally include a double-stranded region forming the 'ligatable' end of the adaptor, e.g., the end that is joined to a double-stranded target nucleic acid in the ligation reaction. The ligatable end of the universal adaptor may be blunt or, in other embodiments, short 5' or 3' overhangs of one or more nucleotides may be present to facilitate/promote ligation. The 5' terminal nucleotide at the ligatable end of the universal adapter is typically phosphorylated to enable phosphodiester linkage to a 3' hydroxyl group on the target polynucleotide.

The term 'unmatched region' refers to a region of the universal adaptor, the region of single-stranded non-complementary nucleic acid strands, wherein the sequences of the two polynucleotide strands forming the universal adaptor exhibit a degree of non-complementarity such that the two strands are not capable of fully annealing to each other under standard annealing conditions for a primer extension or PCR reaction. The unmatched region(s) may exhibit some degree of annealing under standard reaction conditions for an enzyme-catalyzed ligation reaction, provided that the two strands revert to single stranded form under annealing conditions in an amplification reaction.

It is to be understood that the 'unmatched region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridize, and thus form a single stranded region on both strands. The mismatches may also take the form of 'bubbles', wherein both ends of the universal adapter construct(s) are capable of hybridizing to each other and forming a duplex, but the central region is not. The portion of the strand(s) forming the unmatched region are not annealed under conditions in which other portions of the same two strands are annealed to form one or more double-stranded regions. For avoidance of doubt it is to be understood that a single-stranded or single base overhang at the 3' end of a polynucleotide duplex that subsequently undergoes ligation to the target sequences does not constitute an 'unmatched region' in the context of this disclosure.

The lower limit on the length of the unmatched region will typically be determined by function, for example, the need to provide a suitable sequence for i) binding of a primer for primer extension, PCR and/or sequencing (for instance, binding of a primer to a universal primer binding site), or for ii) binding of a universal capture binding sequence to a capture nucleic acid for immobilization of a modified target nucleic acid to a surface. Theoretically there is no upper limit on the length of the unmatched region, except that in general it is advantageous to minimize the overall length of the universal adapter, for example, in order to facilitate separation of unbound universal adapters from modified target nucleic acid constructs following the ligation step. Therefore, it is generally preferred that the unmatched region should be less than 50, or less than 40, or less than 30, or less than 25 consecutive nucleotides in length.

The region of single-stranded non-complementary nucleic acid strands includes at least one universal capture binding sequence at the 3' end. The 3' end of a universal adapter includes a universal capture binding sequence that will hybridize to a capture nucleic acid present at amplification sites of an array. Optionally, the 5' end of a universal adapter includes a second universal capture binding sequence attached to each end of a target nucleic acid, where the second universal capture binding sequence will hybridize to a different capture nucleic acid present at amplification sites of an array.

The region of single-stranded non-complementary nucleic acid strands typically also includes at least one universal primer binding site. A universal primer binding site is a universal sequence that can be used for amplification and/or sequencing of a target nucleic acid ligated to the universal adapter.

The region of single-stranded non-complementary nucleic acid strands can also include at least one index. An index can be used as a marker characteristic of the source of particular target nucleic acids on an array (U.S. Pat. No. 8,053,192). Generally, the index is a synthetic sequence of nucleotides that is part of the universal adapter which is added to the target nucleic acids as part of the library preparation step. Accordingly, an index is a nucleic acid sequence which is attached to each of the target molecules of a particular sample, the presence of which is indicative of, or is used to identify, the sample or source from which the target molecules were isolated. In one embodiment, a dual index system can be used. In a dual index system, the universal adapter attached to target nucleic acids include two different index sequences (U.S. Pat. Pub. No. 2018/0305750, U.S. Pat. Pub. No. 2018/0305751, U.S. Pat. Pub. No. 2018/0305752, and U.S. Pat. Pub. No. 2018/0305753).

Preferably an index may be up to 20 nucleotides in length, more preferably 1-10 nucleotides, and most preferably 4-6 nucleotides in length. A four nucleotide index gives a possibility of multiplexing 256 samples on the same array, a six base index enables 4096 samples to be processed on the same array.

In one embodiment, the universal capture binding sequence is part of the universal adapter when it is ligated to the double-stranded target fragments, and in another embodiment the universal primer extension binding site is added to the universal adapter after the universal adapter is ligated to the double-stranded target fragments. The addition can be accomplished using routine methods, including amplification-based methods such as PCR.

The precise nucleotide sequence of the universal adapters is generally not material to the disclosure and may be selected by the user such that the desired sequence elements are ultimately included in the common sequences of the plurality of different modified target nucleic acids, for example, to provide for the universal capture binding sequences and binding sites for particular sets of universal amplification primers and/or sequencing primers. Additional sequence elements may be included, for example, to provide binding sites for sequencing primers which will ultimately be used in sequencing of target nucleic acids in the library, sequencing of an index, or products derived from amplification of the target nucleic acids in the library, for example on a solid support.

Although the precise nucleotide sequence of the universal adapter is generally non-limiting to the disclosure, the sequences of the individual strands in the unmatched region should be such that neither individual strand exhibits any internal self-complementarity which could lead to self-annealing, formation of hairpin structures, etc. under standard annealing conditions. Self-annealing of a strand in the unmatched region is to be avoided as it may prevent or reduce specific binding of an amplification primer to this strand.

The mismatched adaptors are preferably formed from two strands of DNA, but may include mixtures of natural and non-natural nucleotides (e.g. one or more ribonucleotides) linked by a mixture of phosphodiester and non-phosphodiester backbone linkages.

Ligation and Amplification of Universal Adaptors

Ligation methods are known in the art and use standard methods. Such methods use ligase enzymes such as DNA ligase to effect or catalyze joining of the ends of the two polynucleotide strands of, in this case, the universal adapter and the double-stranded target nucleic acids, such that covalent linkages are formed. The universal adapter may contain a 5'-phosphate moiety to facilitate ligation to the 3'-OH present on the target fragment. The double-stranded target nucleic acid contains a 5'-phosphate moiety, either residual from the shearing process, or added using an enzymatic treatment step, and has been end repaired, and optionally extended by an overhanging base or bases, to give a 3'-OH suitable for ligation. In this context, joining means covalent linkage of polynucleotide strands which were not previously covalently linked. In a particular aspect of the disclosure, such joining takes place by formation of a phosphodiester linkage between the two polynucleotide strands, but other means of covalent linkage (e.g. non-phosphodiester backbone linkages) may be used.

As discussed herein, in one embodiment universal adaptors used in the ligation are complete and include a universal capture binding sequence and other universal sequences, e.g., a universal primer binding site and an index sequence. The resulting plurality of modified target nucleic acids can be used to prepare immobilized samples for sequencing.

Also, as discussed herein, in one embodiment universal adaptors used in the ligation include a universal primer binding site and an index sequence, and do not include a universal capture binding sequence. The resulting plurality of modified target nucleic acids can be further modified to include specific sequences, such as a universal capture binding sequence. Methods for addition of specific sequences, such as a universal capture binding sequence, to universal primers that are ligated to double-stranded target fragments include amplification-based methods such as PCR, and are known in the art and are described in, for instance, Bignell et al. (U.S. Pat. No. 8,053,192) and Gunderson et al. (WO 2016/130704).

In those embodiments where a universal adapter is modified, an amplification reaction is prepared. The contents of an amplification reaction are known by one skilled in the art and include appropriate substrates (such as dNTPs), enzymes (e.g. a DNA polymerase) and buffer components required for an amplification reaction. Generally, amplification reactions require at least two amplification primers, often denoted 'forward' and 'reverse' primers (primer oligonucleotides) that are capable of annealing specifically to a part of the polynucleotide sequence to be amplified, e.g., a modified target nucleic acid, under conditions encountered in the primer annealing step of each cycle of an amplification reaction. It will be appreciated that if the primers contain any nucleotide sequence which does not anneal to the modified target nucleic acids in the first amplification cycle then this sequence may be copied into the amplification products. For instance, the use of primers having universal capture binding sequences, e.g., sequences that do not anneal to the modified target nucleic acids, the universal capture binding sequences will be incorporated into the resulting amplicon.

Amplification primers are generally single stranded polynucleotide structures. They may also contain a mixture of natural and non-natural bases and also natural and non-natural backbone linkages, provided that any non-natural modifications do not preclude function as a primer—that being defined as the ability to anneal to a template polynucleotide strand during conditions of the amplification reaction and to act as an initiation point for synthesis of a new polynucleotide strand complementary to the template strand. Primers may additionally include non-nucleotide chemical modifications, for example, phosphorothioates to increase exonuclease resistance, again provided such that modifications do not prevent primer function.

Amplification to Generate Clusters

An array that includes amplification sites, each of which includes a clonal population (also referred to as a cluster) of amplicons, can be produced using methods known to the person skilled in the art. In one embodiment, isothermal amplification methods are used, and include producing the clonal population of double stranded amplicons from an individual target nucleic acid, either single-stranded or double-stranded, that has seeded the site. In some embodiments the amplification reaction proceeds until a sufficient number of amplicons are generated to fill the capacity of the respective amplification site. Filling an already seeded site to capacity in this way excludes subsequent target nucleic acids from landing at the site, thereby producing a clonal population of amplicons at the site. Thus, it is desirable in some embodiments that the rate at which amplicons are generated to fill the capacity of amplification sites exceeds the rate at which the individual target nucleic acids are transported to the individual amplification sites.

In some embodiments, amplification methods include, but are not limited to, solid-phase amplification. The term "solid-phase amplification" as used herein refers to any polynucleotide amplification reaction carried out on or in association with a solid support such that all or a portion of the amplified products are immobilized on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers are immobilized on the solid support. Solid phase amplification includes, but is not limited to, systems such as arrays, where one primer is anchored to the surface of the array and the other is in free solution; emulsions, where one primer is anchored to a bead and the other is in free solution; and colony formation in solid phase gel matrices, where one primer is anchored to the surface and one is in free solution. In some embodiments, methods that rely on bridge amplification, where both primers are attached to a surface (see, e.g., WO 2000/018957, U.S. Pat. Nos. 7,972,820; 7,790,418 and Adessi et al., Nucleic Acids Research (2000): 28(20): E87) are used. In some embodiments, methods are used that rely on kinetic exclusion, where recombinase-facilitated amplification and isothermal conditions amplify the library (U.S. Pat. Nos. 9,309,502, 8,895,249, 8,071,308). Amplification reactions can be performed thermally or isothermally.

In some embodiments, apparent clonality can be achieved even if an amplification site is not filled to capacity prior to a second target nucleic acid beginning amplification at the site. Under some conditions, amplification of a first target nucleic acid can proceed to a point that a sufficient number of copies are made to effectively outcompete or overwhelm production of copies from a second target nucleic acid that is transported to the site. For example, in an embodiment that uses a bridge amplification process on a circular feature that is smaller than 500 nm in diameter, it has been determined that after 14 cycles of exponential amplification for a first target nucleic acid, contamination from a second target nucleic acid at the same site will produce an insufficient number of contaminating amplicons to adversely impact sequencing-by-synthesis analysis on an Illumina sequencing platform.

Amplification sites in an array need not be entirely clonal in all embodiments. Rather, for some applications, an individual amplification site can be predominantly populated with amplicons from a first target nucleic acid and can also have a low level of contaminating amplicons from a second target nucleic acid. An array can have one or more amplification sites that have a low level of contaminating amplicons so long as the level of contamination does not have an unacceptable impact on a subsequent use of the array. For example, when the array is to be used in a detection application, an acceptable level of contamination would be a level that does not impact signal to noise or resolution of the detection technique in an unacceptable way. Accordingly, apparent clonality will generally be relevant to a particular use or application of an array made by the methods set forth herein. Exemplary levels of contamination that can be acceptable at an individual amplification site for particular applications include, but are not limited to, at most 0.1%, 0.5%, 1%, 5%, 10% or 25% contaminating amplicons. An array can include one or more amplification sites having these exemplary levels of contaminating amplicons. For example, up to 5%, 10%, 25%, 50%, 75%, or even 100% of the amplification sites in an array can have some contaminating amplicons.

In some embodiments, the method of making an array useful in a method described herein can be carried out under conditions wherein the target nucleic acids are transported (e.g. via diffusion) to the amplification sites as amplification is occurring. Thus, some amplification methods can exploit both a relatively slow transport rate and a relatively slow production of a first amplicon relative to subsequent amplicon formation. For instance, an amplification reaction set forth herein can be carried out such that target nucleic acids are transported from solution to amplification sites simultaneously with (i) the producing of a first amplicon, and (ii) the producing of the subsequent amplicons at other sites of the array. In particular embodiments, the average rate at which the subsequent amplicons are generated at the amplification sites can exceed the average rate at which the target nucleic acids are transported from the solution to the amplification sites. In some cases, a sufficient number of amplicons can be generated from a single target nucleic acid at an individual amplification site to fill the capacity of the respective amplification site. The rate at which amplicons are generated to fill the capacity of respective amplification sites can, for example, exceed the rate at which the individual target nucleic acids are transported from the solution to the amplification sites.

A composition for amplifying target nucleic acids at amplification sites, referred to herein as an "amplification reagent," is typically capable of rapidly making copies of target nucleic acids at amplification sites. An amplification reagent used in a method of the present disclosure will generally include a polymerase and nucleotide triphosphates (NTPs). Any of a variety of polymerases known in the art can be used, but in some embodiments it may be preferable to use a polymerase that is exonuclease negative. Examples of nucleic acid polymerases suitable for use in embodiments of the present disclosure include, but are not limited to, DNA polymerase (such as Klenow fragment, T4 DNA polymerase, Bst (Bacillus stearothermophilus) polymerase), thermostable DNA polymerases (such as Taq, Vent, Deep Vent, Pfu, Tfl, and 9° N DNA polymerases) as well as their genetically modified derivatives (see, for instance, U.S. Pat. No. 9,677,057, U.S. Prov. App. No. 62/753,558, and U.S. Prov. App. No. 62/775,662). In some embodiments, an amplification reagent can also include recombinase, accessory protein, and single-stranded DNA binding (SSB) protein for recombinase-facilitated amplification (see, for instance, U.S. Pat. No. 8,071,308).

The NTPs can be deoxyribonucleotide triphosphates (dNTPs) for embodiments where DNA copies are made. Typically, the four native species, dATP, dTTP, dGTP and dCTP, will be present in a DNA amplification reagent; however, analogs can be used if desired. The NTPs can be ribonucleotide triphosphates (rNTPs) for embodiments where RNA copies are made. Typically, the four native species, rATP, rUTP, rGTP and rCTP, will be present in a RNA amplification reagent; however, analogs can be used if desired. NTPs can be modified with a fluorescent or radioactive group. A large variety of synthetically modified nucleic acids have been developed for chemical and biological methods in order to increase the detectability and/or the functional diversity of nucleic acids. These functionalized/modified molecules (e.g., nucleotide analogs) can be fully compatible with natural polymerizing enzymes, maintaining the base pairing and replication properties of the natural counterparts.

In some embodiments, four modified nucleotide triphosphate types, referred to as reversibly blocked nucleotide triphosphates (rbNTPs), are used (see, for instance, U.S. Pat. No. 9,453,258). rbNTPs possess a 3'-terminator that includes, on the 3' ribose position, both alkoxy and azido functionalities which is removable by cleavage with a phosphine reagent, creating a nucleotide that is reversibly blocked and once again functional for further elongation (i.e., fully functional or ff). Fully functional nucleotides, ffNTPs, are commercially available from Illumina, Inc. (San Diego, Calif.) and are exemplary of rbNTPs. In some embodiments, one or more rbNTPs include fluorescent labels attached via linkers. The linkers can include one or more cleavage groups, or no cleavage groups. For example, a linker attaching one or more rbNTPs to a fluorophore may include an azide and/or an alkoxy group, for example on the same carbon, such that the linkers may be cleaved after each incorporation cycle by means of a phosphine reagent as previously referenced, thereby releasing the fluorescent moiety for further sequence elongation.

Other components of the amplification solution are added consequently to the choice of the polymerase, and they are essentially corresponding to compounds known in the art as being effective to support the activity of each polymerase. The concentration of compounds like dimethyl sulfoxide (DMSO), Bovine Serum Albumin (BSA), poly-ethylene glycol (PEG), Betaine, Triton X-100, denaturant (e.g., formamide), or $MgCl_2$ is well known in the prior art as being important to have an optimal amplification, and therefore the operator can easily adjust such concentrations for the methods of the present disclosure on the basis of the examples presented hereafter and the knowledge generally available.

The rate at which an amplification reaction occurs can be increased by increasing the concentration or amount of one or more of the active components of an amplification reaction, for example, the amount or concentration of polymerase, nucleotide triphosphates, or primers. In some cases, the one or more active components of an amplification reaction that are increased in amount or concentration (or otherwise manipulated in a method set forth herein) are non-nucleic acid components of the amplification reaction.

Amplification rate can also be increased in a method set forth herein by adjusting the temperature. For example, the rate of amplification at one or more amplification sites can be increased by increasing the temperature at the site(s) up to a maximum temperature where reaction rate declines due to denaturation or other adverse events. Optimal or desired temperatures can be determined from known properties of the amplification components in use or empirically for a given amplification reaction mixture. Such adjustments can be made based on a priori predictions of primer melting temperature (Tm) or empirically. In certain embodiments the temperature of an amplification reaction is at least 35° C. to no greater than 70° C. For instance, an amplification reaction can be at least 35° C. to no greater than 48° C. In contrast to other methods that determine the sequence of a nucleic acid that is anchored to a surface, the nucleic acids sequenced according to the present disclosure are attached to the surface by hybridization to a nucleic acid that is anchored to the surface. Accordingly, lower temperatures are often preferred.

Following amplification double-stranded amplicons present at the amplification sites can be converted to single-stranded amplicons by subjecting the amplicons to denaturing conditions. Denaturing conditions include, but are not limited to, formamide, heat, or alkali.

Preparation of Immobilized Samples for Sequencing

The result of amplification is a population of clonal amplification products, single-stranded amplicons, at the amplification sites. The single-stranded amplicons are immobilized on the surface of an amplification site at the 5' ends (for instance, see FIG. 1A where a single-stranded amplicon 11 attached to a capture nucleic acid 12, which is attached at the 5' end to an amplification site 10). The amplicons within an amplification site will be clonal and derived from amplification of a single target nucleic acid, or with acceptable levels of one of more other amplicons as described herein.

Figure 1C:
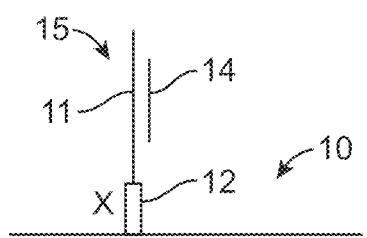
Figure 1F:
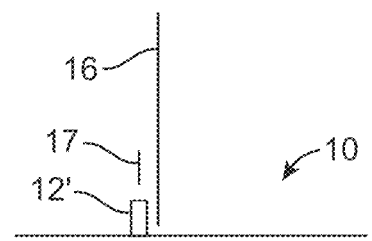
Figure 1D:
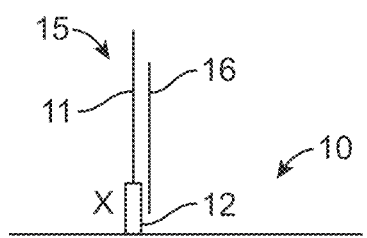

Sequencing of the amplicon is initiated by hybridizing a first sequencing primer to the single-stranded amplicon. Methods for sequencing are described in detail herein. In one embodiment, the first sequencing primer is complementary to a universal sequence present in the 3' region of the amplicon. The sequencing is carried out by the sequential addition of nucleotides, in one embodiment a predetermined number of nucleotides, to the first sequencing primer using the single-stranded amplicon as the template. In some embodiments the sequencing reaction can proceed to the end of the template. In other embodiments, after the sequencing reaction is complete the newly synthesized nucleotide sequence is extended along the remainder of the single-stranded amplicon to the end of the immobilized capture nucleic acid, producing the complementary strand and converting the single-stranded amplicon to a double-stranded structure. For instance, as shown in FIG. 1C, the sequencing primer 13 annealed to the single-stranded amplicon 11 has been extended during the sequencing reaction and integrated into the resulting complementary strand 14. FIG. 1D shows the fully extended complementary strand 16. The complementary strand is not attached to the amplification site.

In one embodiment, the 5' end of the first sequencing primer can be blocked, meaning that the 5' end of the primer is modified to prevent the action of an exonuclease. Blocking of the 5' end can be accomplished in any suitable manner.

To facilitate sequencing of the newly synthesized complementary strand, the capture nucleic acid that is attached to the surface and also attached to the original single-stranded amplicon (e.g., 12 and 11, respectively, in FIG. 1A) is cleaved to allow the optional removal of the original single-stranded amplicon from the double-stranded structure. This cleavage is in the double-stranded region that exists between the capture nucleic acid and the complementary strand, and results in cleavage of only the capture nucleic acid. The cleaving of a nucleotide sequence to permit the optional removal of a specific strand is referred to herein as "linearization." Examples of suitable methods for linearization are described herein and are described in application number WO 2007/010251, U.S. Pat. Nos. 8,431,348, and 8,017,335.

The cleavage site is present in the capture nucleic acid and is typically in a location that results in a substantial portion of the original single-stranded amplicon to be free of the surface of the amplification site—no longer immobilized—and susceptible to loss after the removal step. For instance, as shown in FIG. 1E, the single-stranded amplicon 11 is cleaved at the cleavage site X, leaving a cleaved strand 11' and a shortened capture nucleic acid 12'. The nucleotides at the 3' end of the complementary strand 16 are hybridized to bases of the shortened capture nucleic acid 12', causing the complementary strand 16 to remain associated with the amplification site 10. The person of ordinary skill in the art will appreciate that cleavage site is also typically in a location that results in a shortened capture nucleic acid with enough nucleotides that is sufficient for hybridization with nucleotides at the 3' end of the complementary strand. The cleavage renders the complementary strand available for hybridization of a second sequencing primer and results in the method permitting paired-end sequencing, i.e., the determination of two "reads" of sequence from two places on a single polynucleotide template. Advantageously, the paired-end sequencing possible in the method described herein does not require steps necessary for a paired-end turn, e.g., the use of an amplification site with two different capture nucleic acids and formation of suitable single-stranded templates using the two different capture nucleic acids.

Any suitable enzymatic, chemical or photochemical cleavage reaction can be used to cleave at site X, provided the conditions do not disrupt the hybridization between nucleotides of the shortened capture nucleic acid and the complementary strand. Cleavage can be achieved by, for example, nicking enzyme digestion, in which case the cleavage site is an appropriate restriction site for the enzyme which directs cleavage of the capture nucleic acid; RNase digestion or chemical cleavage of a bond between a deoxyribonucleotide and a ribonucleotide, in which case the cleavage site can include one or more ribonucleotides; chemical reduction of a disulfide linkage with a reducing agent (e.g., TCEP), in which case the cleavage site should include an appropriate disulfide linkage; chemical cleavage of a diol linkage with periodate, in which case the cleavage site should include a diol linkage; and generation of an abasic site and subsequent hydrolysis.

Suitable cleavage techniques for use in the method of the disclosure include, but are not limited to, chemical cleavage, cleavage of an abasic site, cleavage of a ribonucleotide, photochemical cleavage, cleavage of hemimethylated DNA, PCR stoppers, cleavage of a peptide linker, and enzymatic digestion with nicking endonuclease. The person of ordinary skill in the art will recognize that use of some conditions described herein, for instance heat or alkali, may be undesirable in view of the potential for denaturation of the complementary strand from the shortened capture nucleic acid.

Chemical Cleavage

The term "chemical cleavage" encompasses any method which uses a non-nucleic acid and non-enzymatic chemical reagent in order to promote/achieve cleavage of the original single-stranded amplicon. If required, the single-stranded amplicon may include one or more non-nucleotide chemical moieties and/or non-natural nucleotides and/or non-natural backbone linkages in order to permit chemical cleavage reaction. In one embodiment, the capture nucleic acid includes a diol linkage which permits cleavage by treatment with periodate (e.g. sodium periodate). It will be appreciated that more than one diol can be included at the cleavage site.

Diol linker units based on phosphoramidite chemistry suitable for incorporation into a capture nucleic acid are commercially available from Fidelity systems Inc. (Gaithersburg, Md., USA). One or more diol units may be incorporated into a capture nucleic acid using standard methods for automated chemical DNA synthesis. Hence, the capture nucleic acids including one or more diol linkers can be conveniently prepared by chemical synthesis.

The diol linker is cleaved by treatment with a "cleaving agent," which can be any substance which promotes cleavage of the diol. The preferred cleaving agent is periodate, such as aqueous sodium periodate ($NaIO_4$). Following treatment with the cleaving agent (e.g., periodate) to cleave the diol, the cleaved product may be treated with a "capping agent" in order to neutralize reactive species generated in the cleavage reaction. Suitable capping agents for this purpose include amines, such as ethanolamine. Advantageously, the capping agent (e.g., ethanolamine) can be included in a mixture with the cleaving agent (e.g. periodate) so that reactive species are capped as soon as they are formed.

In another embodiment, the capture nucleic acid can include a disulfide group which permits cleavage with a chemical reducing agent, e.g. Tris (2-carboxyethyl)-phosphate hydrochloride (TCEP).

Cleavage of Abasic Sites

An "abasic site" is defined as a position in a nucleic acid from which the base component has been removed. Abasic sites can occur naturally in DNA under physiological conditions by hydrolysis of nucleoside residues, but can also be formed chemically under artificial conditions or by the action of enzymes. Once formed, abasic sites can be cleaved (e.g., by treatment with an endonuclease or other single-stranded cleaving enzyme, exposure to heat or alkali), providing a means for site-specific cleavage the capture nucleic acid. The person of ordinary skill in the art will recognize that use of heat or alkali may be undesirable in view of the potential for denaturation of the complementary strand from the shortened capture nucleic acid.

In one embodiment, an abasic site can be created at a pre-determined position of the capture nucleic acid and then cleaved by first incorporating deoxyuridine (U) at the pre-determined cleavage site. The enzyme uracil DNA glycosylase (UDG) can then be used to remove the uracil base, generating an abasic site. The strand including the abasic site may then be cleaved at the abasic site by treatment with endonuclease (e.g. EndoIV endonuclease, AP lyase, FPG glycosylase/AP lyase, EndoVIII glycosylase/AP lyase), heat or alkali.

Abasic sites may also be generated at non-natural/modified deoxyribonucleotides other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites generated may then be cleaved, typically by treatment with a suitable endonuclease (e.g., EndoIV, AP lyase). Because the non-natural/modified nucleotide is to be incorporated into the capture nucleic acid for use producing the array and amplification of the target nucleic acid, the non-natural/modified nucleotide should be capable of being copied by the polymerase used for the amplification reaction.

In one embodiment, the molecules to be cleaved may be exposed to a mixture containing the appropriate glycosylase and one or more suitable endonucleases. In such mixtures the glycosylase and the endonuclease will typically be present in an activity ratio of at least about 2:1. In a particular embodiment, the USER reagent available from New England Biolabs (NEB #M5505S) is used for the creation of a single nucleotide gap at a uracil base in a capture nucleic acid. Treatment with endonuclease enzymes gives rise to a 3'-phosphate moiety at the cleavage site, which can be removed with a suitable phosphatase such as alkaline phosphatase. For instance, as shown in FIG. 1E, if the cleavage site X is produced using the USER reagent the shortened capture nucleic acid 12' will terminate with a 3'-phosphate group.

Figure 1G:
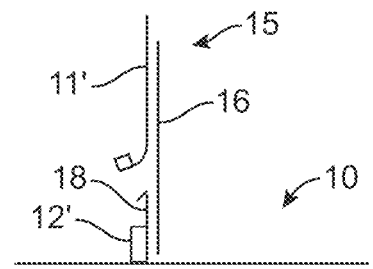

Advantages of this method include the option of releasing a free 3' phosphate group on the cleaved strand, which after phosphatase treatment can provide an initiation point for sequencing a region of the complementary strand (for instance, sequencing a region of strand 16 of FIG. 1G using the shortened capture nucleic acid 12' as the sequencing primer). Because the cleavage reaction requires a residue, e.g., deoxyuridine, which does not occur naturally in DNA, but is otherwise independent of sequence context, if only one non-natural base is included there is no possibility of glycosylase-mediated cleavage occurring elsewhere at unwanted positions in the duplex. Another advantage gained by cleavage of abasic sites in a double-stranded section of an immobilized amplicon generated by action of UDG on uracil is that the first base incorporated in a sequencing-by-synthesis reaction initiating at the free 3' hydroxyl group formed by cleavage will always be T. As a result, for all clonal clusters at different amplification sites of an array which are cleaved in this manner to produce sequencing templates the first base universally incorporated across the whole array will be T. This can provide a sequence-independent assay for individual cluster intensity at the start of a sequencing run.

Cleavage of Ribonucleotides

Incorporation of one or more ribonucleotides into a nucleic acid which is otherwise made up of deoxyribonucleotides (with or without additional non-nucleotide chemical moieties, non-natural bases or non-natural backbone linkages) can provide a site for cleavage using a chemical agent capable of selectively cleaving the phosphodiester bond between a deoxyribonucleotide and a ribonucleotide or using a ribonuclease (RNAse). Therefore, sequencing templates can be produced by cleavage of a capture nucleic acid at a site containing one or more consecutive ribonucleotides using such a chemical cleavage agent or an RNase. In one embodiment, the strand to be cleaved contains a single ribonucleotide to provide a site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$, or $Lu^{3+}$, (Chen et al. Biotechniques. 2002, 32: 518-520; Komiyama et al. Chem. Commun. 1999, 1443-1451)), Fe(3) or Cu(3), or exposure to elevated pH, e.g. treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimize chemical (or enzymatic) cleavage. By way of example, rUMP or rCMP are generally preferred if cleavage is to be carried out by exposure to metal ions, especially rare earth metal ions.

The phosphodiester bond between a ribonucleotide and a deoxyribonucleotide, or between two ribonucleotides may also be cleaved by an RNase. Any endocytic ribonuclease of appropriate substrate specificity can be used for this purpose. For cleavage with ribonuclease it is preferred to include two or more consecutive ribonucleotides, such as from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Capture nucleic acids incorporating one or more ribonucleotides can be readily synthesized using standard techniques for oligonucleotide chemical synthesis with appropriate ribonucleotide precursors.

Photochemical Cleavage

The term "photochemical cleavage" encompasses any method which uses light energy in order to achieve cleavage of the capture nucleic acid. A site for photochemical cleavage can be provided by a non-nucleotide chemical spacer unit in the capture nucleic acid. Suitable photochemical cleavable spacers include the PC spacer phosphoramidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

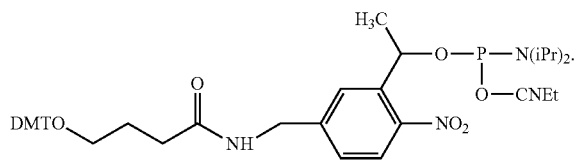

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides.

Cleavage of Hemimethylated DNA

Site-specific cleavage of the capture nucleic acid can also be achieved by incorporating one or more methylated nucleotides into the capture nucleic acid and then cleaving with an endonuclease enzyme specific for a recognition sequence including the methylated nucleotide(s).

The methylated nucleotide(s) in the capture nucleic acid will be opposite of non-methylated deoxyribonucleotides on the complementary strand, such that annealing of the two strands produces a hemimethylated duplex structure. The hemimethylated duplex may then be cleaved by the action of a suitable endonuclease.

Capture nucleic acids incorporating one or methylated nucleotides may be prepared using standard techniques for automated DNA synthesis, using appropriately methylated nucleotide precursors.

Enzymatic Digestion with Nicking Endonuclease

Cleavage of one strand of a double-stranded nucleic acid with a nicking endonuclease is a technique in routine use in the art of molecular biology. Nicking endonucleases are enzymes that selectively cleave or "nick" one strand of a double-stranded nucleic acid and are well known in the art of molecular biology. Essentially any nicking endonuclease may be used, provided that a suitable recognition sequence can be included at the cleavage site present on the capture nucleic acid.

Following cleavage of the capture nucleic acid the sequence of the complementary strand is determined. In one embodiment, this sequencing reaction is initiated by hybridizing a second sequencing primer to the complementary strand. The second sequencing primer can be complementary to a universal sequence present in the 3' region of the amplicon. Typically, the cleaved strand that is hybridized to the complementary strand is removed before the second sequencing primer is hybridized. The cleaved strand can be removed by any suitable method.

In one embodiment, the cleaved strand can be removed enzymatically, such as by use of an exonuclease. In one embodiment, an exonuclease is a 5'-3' DNA exonuclease. Optionally, the 5'-3' DNA exonuclease has a bias for double stranded DNA. Examples of 5' to 3' exonucleases biased for dsDNA include, but are not limited to, T7 exonuclease and exonuclease III (New England Biolabs). Optionally, the 5'-3' DNA exonuclease has a bias for double stranded DNA having a 5' phosphate at the 5' end. Examples of 5' to 3' exonucleases biased for dsDNA having a 5' phosphate at the 5' end include, but are not limited to, lambda exonuclease (New England Biolabs). The person of ordinary skill will recognize that denaturation can be used to remove the cleaved strand, but will require careful consideration of conditions because the hybridization between the shortened capture nucleic acid and the complementary strand needs to be maintained to permit sequencing of the complementary strand.

In another embodiment, the sequencing reaction to determine the sequence of the complementary strand is initiated by using the 3' end of the shortened capture nucleic acid as the second sequencing primer. The sequencing is carried out by the sequential addition of nucleotides, such as a predetermined number of nucleotides, to the second sequencing primer using the complementary strand as the template. In this aspect of the disclosure, removal of the cleaved strand is optional. In one embodiment, the sequence of the complementary strand can be determined by using a DNA polymerase with strand displacing activity. In another embodiment, the cleaved strand can be removed as described herein and a DNA polymerase without displacing activity can be used.

Methods of Sequencing

An array of the present disclosure, for example, having been produced by a method set forth herein and including amplified target nucleic acids at amplification sites, can be used for any of a variety of applications. A particularly useful application is nucleic acid sequencing. One example is sequencing-by-synthesis (SBS). In SBS, extension of a nucleic acid primer along a nucleic acid template (e.g., a target nucleic acid or amplicon thereof) is monitored to determine the sequence of nucleotides in the template. The underlying chemical process can be polymerization (e.g., as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template. A plurality of different templates at different sites of an array set forth herein can be subjected to an SBS technique under conditions where events occurring for different templates can be distinguished due to their location in the array.

Flow cells provide a convenient format for housing an array that is produced by the methods of the present disclosure and that is subjected to an SBS or other detection technique that involves repeated delivery of reagents in cycles. For example, to initiate a first SBS cycle, one or more labeled nucleotides, DNA polymerase, etc., can be flowed into/through a flow cell that houses an array of nucleic acid templates. Those sites of an array where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., Nature 456: 53-59 (2008), WO 04/018497; U.S. Pat. No. 7,057,026; WO 91/06678; WO 07/123,744; U.S. Pat. Nos. 7,329,492; 7,211,414; 7,315,019; 7,405,281, and 8,343,746.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568 and 6,274,320). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence-based detection systems are not necessary for pyrosequencing procedures. Useful fluidic systems, detectors and procedures that can be used for application of pyrosequencing to arrays of the present disclosure are described, for example, in WIPO Published Pat. App. 2012/058096, US 2005/0191698 A1, U.S. Pat. Nos. 7,595,883, and 7,244,559.

Sequencing-by-ligation reactions are also useful including, for example, those described in Shendure et al. Science 309:1728-1732 (2005); U.S. Pat. Nos. 5,599,675; and 5,750,341. Some embodiments can include sequencing-by-hybridization procedures as described, for example, in Bains et al., Journal of Theoretical Biology 135(3), 303-7 (1988); Drmanac et al., Nature Biotechnology 16, 54-58 (1998); Fodor et al., Science 251(4995), 767-773 (1995); and WO 1989/10977. In both sequencing-by-ligation and sequencing-by-hybridization procedures, template nucleic acids (e.g., a target nucleic acid or amplicons thereof) that are present at sites of an array are subjected to repeated cycles of oligonucleotide delivery and detection. Fluidic systems for SBS methods as set forth herein or in references cited herein can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can use methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008).

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1. Methods set forth herein for amplifying target nucleic acids using exclusion amplification can be readily applied to substrates used for detecting protons. More specifically, methods set forth herein can be used to produce clonal populations of amplicons at the sites of the arrays that are used to detect protons.

A useful application for an array of the present disclosure, for example, having been produced by a method set forth herein, is gene expression analysis. Gene expression can be detected or quantified using RNA sequencing techniques, such as those referred to as digital RNA sequencing. RNA sequencing techniques can be carried out using sequencing methodologies known in the art such as those set forth above. Gene expression can also be detected or quantified using hybridization techniques carried out by direct hybridization to an array or using a multiplex assay, the products of which are detected on an array. An array of the present disclosure, for example, having been produced by a method set forth herein, can also be used to determine genotypes for a genomic DNA sample from one or more individual. Exemplary methods for array-based expression and genotyping analysis that can be carried out on an array of the present disclosure are described in U.S. Pat. Nos. 7,582,420; 6,890,741; 6,913,884 or 6,355,431 or US Pat. Pub. Nos. 2005/0053980 A1; 2009/0186349 A1 or US 2005/0181440 A1.

Another useful application for an array having been produced by a method set forth herein is single-cell sequencing. When combined with indexing methods single cell sequencing can be used in chromatin accessibility assays to produce profiles of active regulatory elements in thousands of single cells, and single cell whole genome libraries can be produced. Examples for single-cell sequencing that can be carried out on an array of the present disclosure are described in U.S. Published Patent Application 2018/0023119 A1. U.S. Provisional Applications Ser. Nos. 62/673,023 and 62/680,259.

The methods set forth herein provide for rapid and efficient creation of arrays from any of a variety of nucleic acid libraries. Accordingly the present disclosure provides integrated systems capable of making an array using one or more of the methods set forth herein and further capable of detecting nucleic acids on the arrays using techniques known in the art such as those exemplified above. Thus, an integrated system of the present disclosure can include fluidic components capable of delivering amplification reagents to an array of amplification sites such as pumps, valves, reservoirs, fluidic lines and the like. A particularly useful fluidic component is a flow cell. A flow cell can be configured and/or used in an integrated system to create an array of the present disclosure and to detect the array. Exemplary flow cells are described, for example, in US 2010/0111768 A1 and U.S. Pat. No. 8,951,781. As exemplified for flow cells, one or more of the fluidic components of an integrated system can be used for an amplification method and for a detection method. Taking a nucleic acid sequencing embodiment as an example, one or more of the fluidic components of an integrated system can be used for an amplification method set forth herein and for the delivery of sequencing reagents in a sequencing method such as those exemplified above. Alternatively, an integrated system can include separate fluidic systems to carry out amplification methods and to carry out detection methods. Examples of integrated sequencing systems that are capable of creating arrays of nucleic acids and also determining the sequence of the nucleic acids include, without limitation, the MiSeq™, HiSeq™, NextSeq™, MiniSeq™, NovaSeq™ and iSeq™ sequencing platforms from Illumina, Inc. (San Diego, Calif.) and devices described in U.S. Pat. No. 8,951,781. Such devices can be modified to make arrays using exclusion amplification in accordance with the guidance set forth herein.

A system capable of carrying out a method set forth herein need not be integrated with a detection device. Rather, a stand-alone system or a system integrated with other devices is also possible. Fluidic components similar to those exemplified above in the context of an integrated system can be used in such embodiments.

A system capable of carrying out a method set forth herein, whether integrated with detection capabilities or not, can include a system controller that is capable of executing a set of instructions to perform one or more steps of a method, technique or process set forth herein. For example, the instructions can direct the performance of steps for creating an array under exclusion amplification conditions. Optionally, the instructions can further direct the performance of steps for detecting nucleic acids using methods set forth previously herein. A useful system controller may include any processor-based or microprocessor-based system, including systems using microcontrollers, reduced instruction set computers (RISC), application specific integrated circuits (ASICs), field programmable gate array (FPGAs), logic circuits, and any other circuit or processor capable of executing functions described herein. A set of instructions for a system controller may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The software may be in various forms such as system software or application software. Further, the software may be in the form of a collection of separate programs, or a program module within a larger program or a portion of a program module. The software also may include modular programming in the form of object-oriented programming.

It will be understood that an array of the present disclosure, for example, having been produced by a method set forth herein, need not be used for a detection method. Rather, the array can be used to store a nucleic acid library. Accordingly, the array can be stored in a state that preserves the nucleic acids therein. For example, an array can be stored in a desiccated state, frozen state (e.g. in liquid nitrogen), or in a solution that is protective of nucleic acids. Alternatively, or additionally, the array can be used to replicate a nucleic acid library. For example, an array can be used to create replicate amplicons from one or more of the sites on the array.

Compositions

During or following performance of a method described herein different compositions can result.

In one embodiment, a composition includes an array of amplification sites that include a plurality of clonal double-stranded amplicons. Each double-stranded amplicon includes a first strand attached to the surface of the amplification site by the 5' end, and also includes a break in the backbone. Each double-stranded amplicon also includes a second strand that is not attached to the surface of the amplification site, and nucleotides that are complementary to and hybridized with nucleotides of the first strand (see, for instance, FIG. 1E). The break in the backbone of the first strand is flanked on both sides by complementary nucleotides of the second strand (see, for instance, FIG. 1E, where 11' and 12' make up the first strand and 16 is the second strand). The double-stranded amplicon can be partially double-stranded, e.g., in some embodiments nucleotides at the 3' end of the first strand are not hybridized to nucleotides of the second strand.

EXEMPLARY EMBODIMENTS

Embodiment 1. A method for pairwise sequencing of first and second regions of a target nucleic acid, wherein the first and second regions are in complementary strands of the target nucleic acid, the method comprising:

(a) providing an array comprising a plurality of amplification sites,
wherein the amplification sites comprise (i) a plurality of capture nucleic acids, and (ii) a plurality of clonal single-stranded amplicons,
wherein each single-stranded amplicon is attached at its 5' end to a capture nucleic acid
wherein the capture nucleic acids comprise a cleavage site;

(b) hybridizing a first sequencing primer to a universal sequence present on each single-stranded amplicon;

(c) carrying out a first sequencing reaction by sequential addition of nucleotides to the first sequencing primer using the single-stranded amplicon as a first template to determine the sequence of a first region and to produce a complementary strand of the first region;

(d) extending the complementary strand of the first region to form a double-stranded amplicon that comprises the first sequencing primer, nucleotides incorporated during the sequencing reaction, and nucleotides incorporated during the extending;

(e) cleaving the capture nucleic acid attached to the single-stranded amplicons, wherein the cleavage converts the single-stranded amplicons into (i) shortened capture nucleic acids and (ii) unattached first templates that are not attached at the 5' end to the capture nucleic acid;

(f) carrying out a second sequencing reaction by sequential addition of nucleotides to a second sequencing primer hybridized to the complementary strand and using the complementary strand as a second template to determine the sequence of a second region.

Embodiment 2. The method of Embodiment 1, wherein the cleavage site permits enzymatic, chemical, or photochemical cleavage.

Embodiment 3. The method of Embodiment 2 or 3, wherein cleavage site is a site for cleavage with a nicking endonuclease.

Embodiment 4. The method of any one of Embodiments 1-3, wherein the cleaving comprises contacting the array with a composition comprising at least one enzyme to produce an abasic site at the cleavage site,
wherein cleavage occurs at the cleavage site.

Embodiment 5. The method of any one of Embodiments 1-4, wherein the capture nucleic acids comprise a uracil base or an 8-oxo-guanine base.

Embodiment 6. The method of any one of Embodiments 1-5, wherein the at least one enzyme to produce an abasic site at the cleavage site comprises uracil DNA glycosylase and an endonuclease selected from DNA glycosylase-lyase Endonuclease VIII or FpG glycosylase.

Embodiment 7. The method of any one of Embodiments 1-6, wherein the first sequencing primer is in solution.

Embodiment 8. The method of any one of Embodiments 1-7, wherein the 5' end of the first sequencing primer is blocked.

Embodiment 9. The method of any one of Embodiments 1-8, wherein the second sequencing primer comprises the 3' end of the cleavage site.

Embodiment 10. The method of any one of Embodiments 1-9, wherein the cleaving with an enzyme results in the 3' end of the cleavage sites terminating with a 3'-phosphate, the method further comprising contacting the array with a phosphatase to result in the cleavage sites terminating with a 3'-OH.

Embodiment 11. The method of any one of Embodiments 1-10, wherein the second sequencing reaction comprises use of a DNA polymerase with strand displacing activity.

Embodiment 12. The method of any one of Embodiments 1-11, wherein the second sequencing primer is in solution.

Embodiment 13. The method of any one of Embodiments 1-12, wherein the second sequencing reaction comprises subjecting the cleaved double-stranded amplicons to conditions that remove the unattached first templates, and hybridizing the second sequencing primer to a universal sequence present on the complementary strands.

Embodiment 14. The method of any one of Embodiments 1-13, wherein the removal of the unattached first templates comprises contacting the array with an exonuclease comprising a 5' to 3' exonuclease activity.

Embodiment 15. The method of any one of Embodiments 1-14, wherein the exonuclease is T7 exonuclease.

Embodiment 16. The method of any one of Embodiments 1-15, wherein at least 95% of the amplification sites on the array comprise clonal single-stranded amplicons derived from amplification of different single target nucleic acids.

Embodiment 17. The method of any one of Embodiments 1-16, wherein the first sequencing reaction determines sequences of regions of the single-stranded amplicons, wherein the second sequencing reaction determines sequences of regions of the complementary strands, and wherein the regions of the single-stranded amplicons are complementary to the regions of the complementary strands.

Embodiment 18. The method of any one of Embodiments 1-17, wherein the first sequencing reaction determines sequences of regions of the single-stranded amplicons, wherein the second sequencing reaction determines sequences of regions of the complementary strands, and wherein the regions of the single-stranded amplicons are not complementary to the regions of the complementary strands.

Embodiment 19. The method of any one of Embodiments 1-18, wherein the nucleotides incorporated during (d) or (f) comprise fully functional nucleotides.

Embodiment 20. The method of any one of Embodiments 1-19, wherein the first sequencing reaction comprises sequential addition of a predetermined number of nucleotides to the first sequencing primer.

Embodiment 21. The method of any one of Embodiments 1-20, wherein the second sequencing reaction comprises sequential addition of a predetermined number of nucleotides to the second sequencing primer.

Embodiment 22. The method of any one of Embodiments 1-21, wherein the capture nucleic acids, the first sequencing primer, or the second sequencing primer comprise at least one non-nucleotide chemical moiety, non-naturally occurring nucleotide, or non-naturally occurring backbone linkage.

Embodiment 23. The method of any one of Embodiments 1-22, wherein the single-stranded amplicons comprise two indexes.

Embodiment 24. The method of any one of Embodiments 1-23, further comprising sequencing the indexes.

Embodiment 25. The method of any one of Embodiments 1-24, wherein the first index is sequenced after (c).

Embodiment 26. The method of any one of Embodiments 1-25, wherein the second index is sequenced after (f).

Embodiment 27. The method of any one of Embodiments 1-26, wherein the array is produced by a method comprising:
  (a) providing an amplification reagent comprising
    (i) the array of amplification sites,
    (ii) a solution comprising a plurality of different target nucleic acids and a primer,
  wherein each of the amplification sites comprises the plurality of capture nucleic acids capable of hybridizing to a universal sequence present on the different target nucleic acids in the solution,
  wherein the number of the different target nucleic acids in the solution exceeds the number of amplification sites in the array,
  wherein the different target nucleic acids have fluidic access to the plurality of amplification sites, and
  wherein each of the amplification sites comprises a capacity for several nucleic acids in the plurality of different target nucleic acids; and
  (b) reacting the amplification reagent to produce a plurality of amplification sites that each comprise a clonal population of double-stranded amplicons from an individual target nucleic acid from the solution,
  wherein the double-stranded amplicons comprise a first strand that is attached at its 5' end to a capture nucleic acid and a second strand that is not attached to the amplification site,
  wherein the reacting comprises simultaneously
    (i) transporting the different target nucleic acids to the amplification sites at an average transport rate, and (ii) amplifying the target nucleic acids that are at the amplification sites at an average amplification rate, wherein the average amplification rate exceeds the average transport rate.

Embodiment 28. The method of any one of Embodiments 1-27, further comprising subjecting the double-stranded amplicons to conditions that remove the second strand that is not attached to the amplification site.

Embodiment 29. The method of any one of Embodiments 1-28, wherein the conditions that remove the second strand comprise a denaturant.

Embodiment 30. The method of any one of Embodiments 1-29, wherein the denaturant comprises formamide.

Embodiment 31. The method of any one of Embodiments 1-30, wherein the solution comprises a molecular crowding agent.

Embodiment 32. The method of any one of Embodiments 1-31, wherein the primer hybridizes to a universal sequence present on each single-stranded amplicon.

Embodiment 33. A composition comprising an array of amplification sites,
    wherein amplification sites comprise a plurality of clonal double-stranded amplicons,
    wherein each double-stranded amplicon comprises a first strand attached to the surface of the amplification site by the 5' end and comprising a break in the backbone, and a second strand that is not attached to the surface of the amplification site and comprises nucleotides that are complementary to and hybridized to nucleotides of the first strand,
    wherein the break in the backbone of the first strand is flanked on both sides by complementary nucleotides of the second strand.

Embodiment 34. The composition of Embodiment 33, wherein at least 95% of the amplification sites on the array comprise clonal single-stranded amplicons.

Embodiment 35. The composition of Embodiments 33 or 34, wherein the break in the backbone comprises a break in first strand comprises at least one missing a phosphodiester bond.

Embodiment 36. The composition of any one of Embodiments 33-35, wherein the first strand comprises non-naturally occurring backbone linkage.

Embodiment 37. The composition of any one of Embodiments 33-36, wherein the break in the backbone comprises a break in first strand comprises at least one missing non-naturally occurring backbone linkage.

Embodiment 38. The composition of any one of Embodiments 33-37, wherein break in the backbone comprises at least one abasic site.

Embodiment 39. The composition of any one of Embodiments 33-38, wherein the second strand is complementary to less than all nucleotides of the first strand Embodiment 40. The composition of any one of Embodiments 33-39, wherein the 5' end of the second strand comprises a 5' block.

Embodiment 41. The composition of any one of Embodiments 33-40, wherein the break in the backbone is located from 5 to 50 nucleotides from the attached 5' end.

Embodiment 42. The composition of any one of Embodiments 33-41, wherein the first strand comprises at least 5 nucleotides located 5' of the break that are hybridized to the second strand.

Embodiment 43. A compound, composition, or method including one or more features described herein.

EXAMPLES

The present disclosure is illustrated by the following examples. It is to be understood that the particular examples, materials, amounts, and procedures are to be interpreted broadly in accordance with the scope and spirit of the disclosure as set forth herein.

Example 1

General Assay Methods and Conditions

Unless otherwise noted, this describes the general assay conditions used in the Examples described herein.

Experiments were run using v2.5 HiSeqX flowcells (ILMN) on a cBot (ILMN). During the experiments various enzyme mixes were pumped into the flowcell and incubated at 37° C. for 15 mins. T7 Exonuclease, USER enzymes, and FpG (PLM2v2) were supplied by New England Biolabs. Sequencing was carried out on a HiSeq™ X system (Illumina, Inc., San Diego, Calif.), according to manufacturer instructions.

The P7 primer included an 8-oxoguanine cleavage site cleavable by FpG glycosylase. The P5 primer included a uracil cleavage site cleavable by the USER enzymes.

Read 1

Amplification sites of lanes of a HiSeqX™ flowcell were coated with either the single primer P7 or both P5 and P7 primers using standard methods. Amplification sites were seeded by adding 300 pM of single stranded DNA to all lanes and then amplifying. The lanes with both primers attached to the amplification sites were amplified with 30 mins of exclusion amplification using EPX mix (Illumina, San Diego, Calif.). The lanes with the single primer attached to the amplification sites were amplified with 30 mins of exclusion amplification using EPX mix supplemented with the second primer, P5 in solution. The P5 primer in solution was needed for amplification in single surface primer lanes. Following amplification, some lanes were linearized with USER reagent. A read 1 (R1) primer was added to each lane. Digestion of the 5' end of the R1 primer was expected upon exposure to T7 exonuclease in a later step, so the 5' end of the primers was blocked. One R1 primer was SBS3+T, a standard R1 sequencing primer, and the other R1 primer was the SBS3+T primer modified to include two biotins (bio-P5-SBS3+T). A standard 1×36 cycle HiSeqX sequencing run was used.

Read 2

After the read 1 from single primer clusters, the flowcell was processed for read 2 on a cBot, and then sequenced. In some lanes the strand synthesized by extension from the R1 primer was further extended using AMX mix (Bst amplification mix, (Illumina, San Diego, Calif.). Following extension, the P7 primer was cleaved at the cleavage site, and the resulting strand located on the 3' side of the cleavage site was removed by T7 exonuclease. A read 2 (R2) primer was added to each lane, and a standard 1×36 cycle HiSeqX sequencing run was used. In one lane T7 exonuclease was replaced with T4 kinase to convert the 3' phosphate at the 3' side of the cleavage site to 3' OH, and the sequencing run was done without addition of the R2 primer. All sequencing runs were done at low temperature (45° C.) to reduce dehybrization of the strands during sequencing, and show reasonable intensity, PF and quality metrics.

Second Read 2

To further evaluate the hypothetical structures occurring during the workflow, the flowcell was removed from the sequencer after read 2 (R2) and exposed to NaOH to denature the clusters. The R1 or R2 primer was added to the lanes again, and another sequencing run was done using the same conditions.

Example 2

Single Primer Clusters Provide Useful Sequence Data with the First Read

The single surface primer clusters in lanes 4 (SBS3+T primer), 5 (bio-P5-SBS3+T primer), 6 (SBS3+T primer) and 8 (bio-P5-SBS3+T primer) yielded useful sequence data, showing that the single primer clusters provided useful sequence data with the first read primer (FIG. 2). The single surface primer clusters (lanes 1-3) exhibited higher intensity than the results from the dual primer clusters but lower PF. The higher intensity was likely due to higher effective surface primer density, and the lower PF was likely due to the use of DNA concentrations that had not been optimized for this new process. The data also indicate the different primers behaved the same. Lane 7 failed to pump on the cBot, so is a fluidics failure.

Example 3

Single Primer Clusters Provide Useful Sequence Data with the Second Read, in the Presence and the Absence of the Second Read Primer FIG. 3 shows the results of sequencing with R2. Those lanes with the single primer amplification sites and the process that included strand removal by T7 exonuclease yielded useful sequence data (lanes 4 and 5, and FIG. 4A). This is the first evidence for R2 information from single surface primer clusters. The lane that did not include the R2 primer, Lane 6, also showed some evidence for sequencing from the cleavage site.

The second sequencing run showed that the only lanes which recovered were lane 1 (control lane, rehybridized with the R1 primer) and lane 5 (not NaOH denatured and no R1 primer added, so at cycle 37+ of read 2 still). All other lanes were blank because the strands which were only being kept in place via hybridization to the surface P7 primer were removed by denaturation.

Lane 6 also showed some evidence for sequencing from a nick, as in this lane the clusters were extended with AMX, cleaved with FpG and then the 3' phosphate in the nick converted to 3' OH via a T4 kinase step. The PF from this lane is ~0 due to the sequence going through a mono-template area of our clusters, but the intensity by cycle trace shows the expected sequence up to ~cycle 20 (FIG. 4B).

Example 4

Denaturation and Subsequent R2 Sequencing of Those Lanes with Predicted Attachment by Hybridization Result in No Signal As a control to evaluate whether the expected sequence data was obtained, the flowcell was taken off the sequencer after the read 2, and "rehybed" using NaOH to denature the clusters before hybridization of the R2 primer. FIG. 5 shows that the only lanes which recovered after the rehyb were lane 1 (control lane, rehybed with R1 primer) and lane 5 (not NaOH denatured or hybed, so at cycle 37+ of read 2 still). All other lanes were blank because we have dehybed the strands which were only being kept in place via hybridization to the surface P7 oligo.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present disclosure. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The invention claimed is:

1. A method for pairwise sequencing of first and second regions of a target nucleic acid, wherein the first and second regions are in complementary strands of the target nucleic acid, the method comprising:
    (a) providing an array comprising a plurality of amplification sites,
    wherein the amplification sites comprise (i) a plurality of capture nucleic acids, and (ii) a plurality of clonal single-stranded amplicons,
    wherein each single-stranded amplicon is attached at its 5' end to a capture nucleic acid,
    wherein the capture nucleic acids comprise a cleavage site;
    (b) hybridizing a first sequencing primer to a universal sequence present on each single-stranded amplicon;
    (c) carrying out a first sequencing reaction by sequential addition of nucleotides to the first sequencing primer using the single-stranded amplicon as a first template to determine the sequence of a first region and to produce a complementary strand of the first region;

(d) extending the complementary strand of the first region to form a double-stranded amplicon that comprises the first sequencing primer, nucleotides incorporated during the sequencing reaction, and nucleotides incorporated during the extending;

(e) cleaving the capture nucleic acids attached to the single-stranded amplicons, wherein the cleavage converts the single-stranded amplicons into (i) shortened capture nucleic acids and (ii) unattached first templates that are not attached at the 5' end to the capture nucleic acids; and (f) carrying out a second sequencing reaction by sequential addition of nucleotides to a second sequencing primer hybridized to the complementary strand and using the complementary strand as a second template to determine the sequence of a second region, wherein the second sequencing primer is in solution, wherein the complementary strand is not attached to the surface of the amplification site, and wherein the second sequencing reaction comprises subjecting the cleaved double-stranded amplicons to conditions that remove the unattached first templates, and hybridizing the second sequencing primer to a universal sequence present on the complementary strands.

2. The method of claim 1, wherein the cleavage site permits enzymatic, chemical, or photochemical cleavage.

3. The method of claim 2, wherein the cleavage site is a site for cleavage with a nicking endonuclease.

4. The method of claim 2, wherein the cleaving comprises contacting the array with a composition comprising at least one enzyme to produce an abasic site at the cleavage site, wherein cleavage occurs at the cleavage site.

5. The method of claim 4, wherein the capture nucleic acids comprise a uracil base or an 8-oxo-guanine base.

6. The method of claim 4, wherein the at least one enzyme to produce an abasic site at the cleavage site comprises uracil DNA glycosylase and an endonuclease selected from DNA glycosylase-lyase Endonuclease VIII or FpG glycosylase.

7. The method of claim 1, wherein the first sequencing primer is in solution.

8. The method of claim 7, wherein the 5' end of the first sequencing primer is blocked.

9. The method of claim 1, wherein the second sequencing primer comprises the 3' end of the cleavage site.

10. The method of claim 6, wherein the cleaving with an enzyme results in the 3' end of the cleavage sites terminating with a 3'-phosphate, the method further comprising contacting the array with a phosphatase to result in the cleavage sites terminating with a 3'-OH.

11. The method of claim 9, wherein the second sequencing reaction comprises use of a DNA polymerase with strand displacing activity.

12. The method of claim 1, wherein the removal of the unattached first templates comprises contacting the array with an exonuclease comprising a 5' to 3' exonuclease activity.

13. The method of claim 12, wherein the exonuclease is T7 exonuclease.

14. The method of claim 1, wherein at least 95% of the amplification sites on the array comprise clonal single-stranded amplicons, wherein the amplicons of each amplification site are derived from amplification of a different single target nucleic acids.

15. The method of claim 1, wherein the first sequencing reaction determines sequences of regions of the single-stranded amplicons, wherein the second sequencing reaction determines sequences of regions of the complementary strands, and wherein the regions of the single-stranded amplicons are complementary to the regions of the complementary strands.

16. The method of claim 1, wherein the first sequencing reaction determines sequences of regions of the single-stranded amplicons, wherein the second sequencing reaction determines sequences of regions of the complementary strands, and wherein the regions of the single-stranded amplicons are not complementary to the regions of the complementary strands.

17. The method of claim 1, wherein the nucleotides incorporated during (d) or (f) comprise fully functional nucleotides.

18. The method of claim 1, wherein the first sequencing reaction comprises sequential addition of a predetermined number of nucleotides to the first sequencing primer.

19. The method of claim 1, wherein the second sequencing reaction comprises sequential addition of a predetermined number of nucleotides to the second sequencing primer.

20. The method of claim 1, wherein the capture nucleic acids, the first sequencing primer, or the second sequencing primer comprise at least one non-nucleotide chemical moiety, non-naturally occurring nucleotide, or non-naturally occurring backbone linkage.

21. The method of claim 1, wherein the single-stranded amplicons comprise a first index and a second index.

22. The method of claim 21, further comprising sequencing the indexes.

23. The method of claim 22, wherein the first index is sequenced after (c).

24. The method of claim 22, wherein the second index is sequenced after (f).

25. The method of claim 1, wherein the array is produced by a method comprising:

(a) providing an amplification reagent comprising
(i) the array of amplification sites,
(ii) a solution comprising a plurality of different target nucleic acids and a primer,
wherein each of the amplification sites comprises the plurality of capture nucleic acids capable of hybridizing to a universal sequence present on the different target nucleic acids in the solution,
wherein the number of the different target nucleic acids in the solution exceeds the number of amplification sites in the array,
wherein the different target nucleic acids have fluidic access to the plurality of amplification sites, and
wherein each of the amplification sites comprises a capacity for several nucleic acids in the plurality of different target nucleic acids; and (b) reacting the amplification reagent to produce a plurality of amplification sites that each comprise a clonal population of double-stranded amplicons from an individual target nucleic acid from the solution,
wherein the double-stranded amplicons comprise a first strand that is attached at its 5' end to a capture nucleic acid and a second strand that is not attached to the amplification site,
wherein the reacting comprises simultaneously
(i) transporting the different target nucleic acids to the amplification sites at an average transport rate, and (ii) amplifying the target nucleic acids that are at the amplification sites at an average amplification rate, wherein the average amplification rate exceeds the average transport rate.

26. The method of claim 25, further comprising subjecting the double-stranded amplicons to conditions that remove the second strand that is not attached to the amplification site.

27. The method of claim 26, wherein the conditions that remove the second strand comprise a denaturant.

28. The method of claim 27, wherein the denaturant comprises formamide.

29. The method of claim 25, wherein the solution comprises a molecular crowding agent.

30. The method of claim 25, wherein the primer hybridizes to a universal sequence present on each single-stranded amplicon.

* * * * *

UNITED STATES PATENT AND TRADEMARK OFFICE
CERTIFICATE OF CORRECTION

PATENT NO. : 11,634,765 B2
APPLICATION NO. : 16/717303
DATED : April 25, 2023
INVENTOR(S) : Jonathan Mark Boutell and Pietro Gatti-Lafranconi Page 1 of 1

It is certified that error appears in the above-identified patent and that said Letters Patent is hereby corrected as shown below:

In the Claims

Column 41, Line 65:
In Claim 14, delete "acids." and insert -- acid. --.

Signed and Sealed this
Fourth Day of July, 2023

Katherine Kelly Vidal
*Director of the United States Patent and Trademark Office*